US009203113B2

(12) United States Patent
Miyoshi et al.

(10) Patent No.: US 9,203,113 B2
(45) Date of Patent: Dec. 1, 2015

(54) NONAQUEOUS ELECTROLYTE SOLUTION, ELECTROCHEMICAL ELEMENT USING SAME, AND 1,2-DIOXYPROPANE COMPOUND USED IN SAME

(75) Inventors: Kazuhiro Miyoshi, Yamaguchi (JP); Yuichi Kotou, Yamaguchi (JP); Shoji Shikita, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 447 days.

(21) Appl. No.: 13/634,006

(22) PCT Filed: Mar. 24, 2011

(86) PCT No.: PCT/JP2011/057243
§ 371 (c)(1),
(2), (4) Date: Sep. 11, 2012

(87) PCT Pub. No.: WO2011/122449
PCT Pub. Date: Oct. 6, 2011

(65) Prior Publication Data
US 2013/0004862 A1    Jan. 3, 2013

(30) Foreign Application Priority Data
Mar. 30, 2010   (JP) ................................. 2010-079620

(51) Int. Cl.
*H01M 10/0567*   (2010.01)
*H01M 4/131*   (2010.01)
(Continued)

(52) U.S. Cl.
CPC ......... *H01M 10/0567* (2013.01); *C07D 317/18* (2013.01); *C07D 317/38* (2013.01); *C07D 327/10* (2013.01); *C07D 497/04* (2013.01); *H01M 4/131* (2013.01); *H01M 4/386* (2013.01); *H01M 4/387* (2013.01); *H01M 4/52* (2013.01); *H01M 4/587* (2013.01);
(Continued)

(58) Field of Classification Search
CPC ...................... H01M 10/0567; H01M 10/0569; H01M 10/052; H01M 4/131; H01M 4/52; H01M 4/5825; H01M 4/587; H01M 4/387; H01M 4/386; H01M 2300/0037; Y02E 60/122; Y02T 10/7011
See application file for complete search history.

(56) References Cited

U.S. PATENT DOCUMENTS

2005/0214649 A1   9/2005   Yew et al.
2007/0243471 A1   10/2007   Takahashi
(Continued)

FOREIGN PATENT DOCUMENTS

CN      1841832 A    10/2006
CN    101471436 A    7/2009
(Continued)

OTHER PUBLICATIONS

Combined Chinese Office Action and Search Report issued Aug. 15, 2014 in Patent Application No. 201180011803.1 (with English translation of categories of cited documents).
(Continued)

*Primary Examiner* — Laura Weiner
(74) *Attorney, Agent, or Firm* — Oblon, McClelland, Maier & Neustadt, L.L.P.

(57) ABSTRACT

An object of the present invention is to provide a nonaqueous electrolytic solution capable of improving low-temperature load characteristics after high temperature charging storage, an electrochemical element using it, and a 1,2-dioxypropane compound used for it.

The nonaqueous electrolytic solution of the present invention comprises an electrolyte salt dissolved in a nonaqueous solvent, and contains a 1,2-dioxypropane compound represented by the above-mentioned general formula (I).

(I)

(wherein $R^1$ and $R^2$ each represent a hydrogen atom, or an alkyl group having from 1 to 6 carbon atoms; $X^1$ represents a group selected from —S(=O)—, —S(=O)$_2$—, —C(=O)—, —CR$^3$R$^4$—, —P(=O)(OR$^5$)— and —SiR$^6$R$^7$—; $R^3$ and $R^4$ each represent a hydrogen atom, or an alkyl group having from 1 to 6 carbon atoms; $R^5$ to $R^7$ each represent an alkyl group having from 1 to 6 carbon atoms.

$Y^1$ represents an alkylsulfinyl group, an alkenylsulfinyl group, an alkynylsulfinyl group, an arylsulfinyl group, an alkylsulfonyl group, an alkenylsulfonyl group, an alkynylsulfonyl group, or an arylsulfonyl group;

$Z^1$ represents a hydrogen atom, an alkyl group, an alkylsulfinylmethyl group, an alkenylsulfinylmethyl group, an alkynylsulfinylmethyl group, an arylsulfinylmethyl group, an alkylsulfonylmethyl group, an alkenylsulfonylmethyl group, an alkynylsulfonylmethyl group, or an arylsulfonylmethyl group;

provided that at least one hydrogen atom on the carbon atom of $X^1$, $Y^1$ and $Z^1$ may be substituted with a halogen atom).

19 Claims, No Drawings

(51) Int. Cl.

| | | |
|---|---|---|
| *H01M 4/52* | (2010.01) | |
| *H01M 4/58* | (2010.01) | |
| *H01M 4/587* | (2010.01) | |
| *H01M 4/38* | (2006.01) | |
| *C07D 327/10* | (2006.01) | |
| *H01M 10/052* | (2010.01) | |
| *C07D 317/18* | (2006.01) | |
| *C07D 317/38* | (2006.01) | |
| *C07D 497/04* | (2006.01) | |
| *H01M 10/0569* | (2010.01) | |
| *C07F 9/6574* | (2006.01) | |

(52) U.S. Cl.
CPC ......... *H01M 4/5825* (2013.01); *H01M 10/052* (2013.01); *C07F 9/65742* (2013.01); *H01M 10/0569* (2013.01); *H01M 2300/0037* (2013.01); *Y02E 60/122* (2013.01); *Y02T 10/7011* (2013.01)

(56) References Cited

U.S. PATENT DOCUMENTS

| | | | |
|---|---|---|---|
| 2008/0286648 A1 | 11/2008 | Ihara et al. | |
| 2009/0280414 A1 | 11/2009 | Koh et al. | |
| 2013/0115520 A1* | 5/2013 | Abe et al. | 429/338 |

FOREIGN PATENT DOCUMENTS

| | | |
|---|---|---|
| CN | 101517813 A | 8/2009 |
| JP | 2000 188127 | 7/2000 |
| JP | 2005 285765 | 10/2005 |
| JP | 2007 242545 | 9/2007 |
| JP | 2007 287518 | 11/2007 |
| JP | 2008 147119 | 6/2008 |
| JP | 2010 503974 | 2/2010 |
| WO | WO 2012/011586 * | 1/2012 |

OTHER PUBLICATIONS

CAS No. 82813-85-2, ichemistry.cn, Aug. 28, 2014, 1 Page.
CAS No. 62729-17-3, ichemistry.cn, Aug. 28, 2014, 1 Page.
Kang, S.K., et al., "A New Method for the Dehydration of β-Hydroxy Sulfones: Synthesis of (E,S)-γ-Hydroxy-α, β-unsaturated Sulfones and (S) -ε- Hydroxy-(E,E)-α,γ-dienyl, Sulfones," Journal of the Chemical Society, Perkin Transactions 1, pp. 405 to 406, (1992).
Nabeshima, T., et al., "Facile Synthesis of Thiolariat Ethers or Crown Ethers Containing a Mercapto Group as a Side Arm," Bulleting of the Chemical Society of Japan., vol. 68, No. 1, pp. 227 to 229, (1995).
Dyer, J., et al., "Oxygen-17 Nuclear Magnetic Resonance Spectroscopy of Sulfoxides and Sulfones. Alkyl Substituent Induced Chemical Shift Effects," Journal of Organic Chemistry, vol. 47, No. 19, pp. 3660 to 3664, (1982).
International Search Report Issued Jun. 28, 2011 in PCT/JP11/57243 Filed Mar. 24, 2011.
Extended European Search Report issued Aug. 8, 2013 in Patent Application No. 11762680.4.
Hirotaka Tagoshi et al., "Syntheses and Properties of Polysulfides Containing Spiroorthocarbonate Moiety", Journal of Polymer Science, vol. 27, XP-55070872, 1989, pp. 4169-4179.

* cited by examiner

NONAQUEOUS ELECTROLYTE SOLUTION, ELECTROCHEMICAL ELEMENT USING SAME, AND 1,2-DIOXYPROPANE COMPOUND USED IN SAME

THIS APPLICATION IS A NATIONAL STAGE OF

PCT/JP11/057243 filed Mar. 24, 2011 and claims the benefit of JP2010-079620 filed Mar. 30, 2010.

TECHNICAL FIELD

The present invention relates to a nonaqueous electrolytic solution capable of improving low-temperature load characteristics after high temperature charging storage, an electrochemical element using it, and a 1,2-dioxypropane compound used for it.

BACKGROUND ART

In recent years, electrochemical elements, especially lithium secondary batteries have been widely used as power supplies for small-sized electronic devices such as mobile telephones, notebook-size personal computers and the like, power supplies for electric vehicles, as well as for electric power storage, etc. These electronic devices and vehicles may be used in a broad temperature range, for example, at midsummer high temperatures or at frigid low temperatures, and are therefore required to be improved in point of the charging and discharging cycle properties well balanced in a broad temperature range.

A lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery using a highly-crystalline carbon material such as natural graphite, artificial graphite or the like as the negative electrode material therein, the decomposed product or gas generated through reductive decomposition of the solvent in the nonaqueous electrolytic solution on the surface of the negative electrode during charging detracts from the electrochemical reaction favorable for the battery, therefore worsening the cycle properties of the battery. Deposition of the decomposed product of the nonaqueous solvent interferes with smooth absorption and release of lithium by the negative electrode, and therefore, in particular, the low-temperature load characteristics after high-temperature charging storage may be thereby often worsened.

In addition, it is known that a lithium secondary battery using a lithium metal or its alloy, or a metal elemental substance such as tin, silicon or the like or its metal oxide as the negative electrode material therein may have a high initial battery capacity but the battery capacity and the battery performance thereof such as cycle properties greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the low-temperature load characteristics after high-temperature charging storage may be thereby often worsened.

On the other hand, it is known that, in a lithium secondary battery using, for example, $LiCoO_2$, $LiMn_2O_4$, $LiNiO_2$, $LiFePO_4$ or the like as the positive electrode, when the nonaqueous solvent in the nonaqueous electrolytic solution is heated at a high temperature in the charged state, the decomposed product or the gas thereby locally generated through partial oxidative decomposition in the interface between the positive electrode material and the nonaqueous electrolytic solution interferes with the electrochemical reaction favorable for the battery, and therefore the low-temperature load characteristics after high-temperature charging storage are thereby also worsened.

As in the above, the decomposed product and the gas generated through decomposition of the nonaqueous electrolytic solution on the positive electrode or the negative electrode may interfere with the movement of lithium ions or may swell the battery, and the battery performance is thereby worsened. Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the high-temperature cycle properties and the low-temperature characteristics after high-temperature cycles.

As a lithium primary battery, for example, known is one in which the positive electrode is formed of manganese dioxide or fluorographite and the negative electrode is formed of lithium metal, and the lithium primary battery of the type is widely used as having a high energy density, for which, however, it is desired to prevent the increase in the internal resistance during long-term storage and to improve the long-term storage performance at high temperatures.

Recently, further, as a novel power source for electric vehicles or hybrid electric vehicles, electric storage devices have been developed, for example, an electric double layer capacitor using activated carbon or the like as the electrode from the viewpoint of the output density thereof, and a hybrid capacitor including a combination of the electric storage principle of a lithium ion secondary battery and that of an electric double layer capacitor (an asymmetric capacitor where both the capacity by lithium absorption and release and the electric double layer capacity are utilized) from the viewpoint of both the energy density and the output density thereof; and it is desired to improve the load characteristics after high-temperature charging storage of these capacitors.

Patent Reference 1 discloses an electrolytic solution containing, in a nonaqueous solvent, from 0.1 to 30 parts by weight of a sulfonate compound of which the carbonate skeleton-containing 5-membered ring structure has an oxysulfonyl group at the 4-position thereof via a methylene chain, such as 1,3-dioxan-2-onyl-4-methyl methyl sulfonate (also called 4-(methanesulfonyloxymethyl)-1,3-dioxolan-2-one), saying that the battery containing the electrolytic solution of the type is excellent in cycle properties.

Patent Reference 2 discloses an electrolytic solution containing, in a nonaqueous solvent, from 0.1 to 30 parts by weight of erythritan sulfite of which the sulfite skeleton-containing 5-membered ring structure has an ether oxygen at the 4-position thereof via a methylene chain, saying that the battery containing the electrolytic solution of the type is excellent in cycle properties.

CITATION LIST

Patent References

Patent Reference 1: JP-T 2010-503974
Patent Reference 2: JP-A 2000-188127

SUMMARY OF THE INVENTION

Problems that the Invention is to Solve

An object of the present invention is to provide a nonaqueous electrolytic solution capable of improving low-temperature load characteristics after high temperature charging storage, an electrochemical element using it, and a 1,2-dioxypropane compound used for it.

Means for Solving the Problems

The present inventors have investigated in detail the performance of the nonaqueous electrolytic solutions in the above-mentioned prior art. As a result, the nonaqueous electrolytic solutions of the above-mentioned patent references could not provide a remarkable effect of improving low-temperature load characteristics after high-temperature charging storage.

Given the situation, the present inventors have assiduously studied for the purpose of solving the above-mentioned problems, and have found that, when a specific compound that has a structure where a sulfinyl group (—S(=O)—) or a sulfonyl group (—S(=O)$_2$—) bonds to the 4-position of the 5-membered ring structure thereof having a specific substituent, via a carbon atom therebetween (or that is, having $Y^1$), is added to a nonaqueous electrolytic solution of an electrolyte salt dissolved in a nonaqueous solvent, then the electrolytic solution can improve low-temperature load characteristics after high-temperature charging storage, and have completed the present invention.

Specifically, the present invention provides the following (1) to (3):

(1) A nonaqueous electrolytic solution of an electrolyte salt dissolved in a nonaqueous solvent, which comprises a 1,2-dioxypropane compound represented by the following general formula (I):

[Chemical Formula 1]

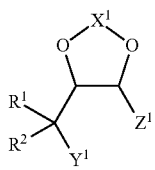

(I)

(In the formula, $R^1$ and $R^2$ each represent a hydrogen atom, or an alkyl group having from 1 to 6 carbon atoms; $X^1$ represents a group selected from —S(=O)—, —S(=O)$_2$—, —C(=O)—, —CR$^3$R$^4$—, —P(=O)(OR$^5$)— and —SiR$^6$R$^7$—; $R^3$ and $R^4$ each represent a hydrogen atom, or an alkyl group having from 1 to 6 carbon atoms; $R^5$ to $R^7$ each represent an alkyl group having from 1 to 6 carbon atoms.

$Y^1$ represents an alkylsulfinyl group having from 1 to 6 carbon atoms, an alkenylsulfinyl group having from 2 to 6 carbon atoms, an alkynylsulfinyl group having from 3 to 6 carbon atoms, an arylsulfinyl group having from 6 to 12 carbon atoms, an alkylsulfonyl group having from 1 to 6 carbon atoms, an alkenylsulfonyl group having from 2 to 6 carbon atoms, an alkynylsulfonyl group having from 3 to 6 carbon atoms, or an arylsulfonyl group having from 6 to 12 carbon atoms;

$Z^1$ represents a hydrogen atom, an alkyl group having from 1 to 4 carbon atoms, an alkylsulfinylmethyl group having from 2 to 7 carbon atoms, an alkenylsulfinylmethyl group having from 3 to 7 carbon atoms, an alkynylsulfinylmethyl group having from 4 to 7 carbon atoms, an arylsulfinylmethyl group having from 7 to 13 carbon atoms, an alkylsulfonylmethyl group having from 2 to 7 carbon atoms, an alkenylsulfonylmethyl group having from 3 to 7 carbon atoms, an alkynylsulfonylmethyl group having from 4 to 7 carbon atoms, or an arylsulfonylmethyl group having from 7 to 13 carbon atoms.

When $Z^1$ is an alkyl group having from 1 to 4 carbon atoms, then $Y^1$ and $Z^1$ may bond to each other to form a ring. At least one hydrogen atom on the carbon atom of $X^1$, $Y^1$ and $Z^1$ may be substituted with a halogen atom.)

(2) An electrochemical element comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of the above (1).

(3) A 1,2-dioxypropane compound represented by the following general formula (II):

[Chemical Formula 2]

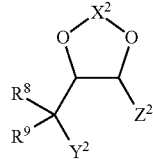

(II)

(In the formula, $R^8$ and $R^9$ each represent a hydrogen atom, or an alkyl group having from 1 to 6 carbon atoms; $X^2$ represents a group selected from —S(=O)—, —S(=O)$_2$—, —C(=O)—, —P(=O)(OR$^{10}$)— and —SiR$^{11}$R$^{12}$—; $R^{10}$ to $R^{12}$ each represent an alkyl group having from 1 to 6 carbon atoms.

$Y^2$ represents an alkylsulfinyl group having from 1 to 4 carbon atoms, an alkenylsulfinyl group having from 2 to 6 carbon atoms, an alkynylsulfinyl group having from 3 to 6 carbon atoms, an alkylsulfonyl group having from 1 to 4 carbon atoms, an alkenylsulfonyl group having from 2 to 6 carbon atoms, or an alkynylsulfonyl group having from 3 to 6 carbon atoms;

$Z^2$ represents a hydrogen atom, a methyl group, an alkylsulfinylmethyl group having from 2 to 7 carbon atoms, an alkylsulfinylmethyl group having from 2 to 7 carbon atoms, an alkenylsulfinylmethyl group having from 3 to 7 carbon atoms, an alkynylsulfinylmethyl group having from 4 to 7 carbon atoms, an alkylsulfonylmethyl group having from 2 to 7 carbon atoms, an alkenylsulfonylmethyl group having from 3 to 7 carbon atoms, or an alkynylsulfonylmethyl group having from 4 to 7 carbon atoms.

At least one hydrogen atom on the carbon atom of $X^2$, $Y^2$ and $Z^2$ may be substituted with a halogen atom.)

Advantage of the Invention

According to the present invention, there are provided a nonaqueous electrolytic solution capable of improving low-temperature load characteristics after high-temperature charging storage, an electrochemical element using it, and a 1,2-dioxypropane compound used for it.

BEST MODE FOR CARRYING OUT THE INVENTION

[Nonaqueous Electrolytic Solution]

The nonaqueous electrolytic solution of the present invention comprises an electrolyte salt dissolved in a nonaqueous solvent, and contains a 1,2-dioxypropane compound represented by the above-mentioned general formula (I).

Though not always clear, the reason why the nonaqueous electrolytic solution of the present invention can remarkably improve low-temperature load characteristics after high-temperature charging storage may be considered as follows:

The 1,2-dioxypropane compound having a sulfinyl group or a sulfonyl group at the 3-position thereof, which is represented by the above-mentioned general formula (I) and which is contained in the nonaqueous electrolytic solution of the present invention, has a structure where a sulfinyl group (—S(=O)—) or a sulfonyl group (—S(=O)$_2$—) having high electron attractivity bonds to the 4-position of the 5-membered ring structure thereof having a specific substituent, via a carbon atom therebetween, and therefore, the 5-membered ring site having a specific substituent of the compound can be readily reduced and decomposed on a negative electrode to form a surface film stable at high temperatures. In addition, it has turned out that the oxygen atom contained in the 5-membered ring structure and the oxygen atom contained in the sulfinyl group or the sulfonyl group could be trap sites for lithium ion, therefore forming a surface film that contains lithium ions in a high concentration and bringing about a specific effect of remarkably improving low-temperature load characteristics even after high-temperature charging storage.

The 1,2-dioxypropane compound contained in the nonaqueous electrolytic solution of the invention is represented by the following general formula (I):

[Chemical Formula 3]

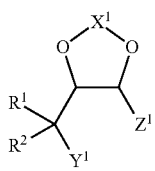
(I)

$R^1$ and $R^2$ in the general formula (I) each represent a hydrogen atom or an alkyl group having from 1 to 6 carbon atoms, preferably a hydrogen atom, a methyl group, an ethyl group, a propyl group, an isopropyl group, a butyl group, a sec-butyl group, a tert-butyl group, a pentyl group, a hexyl group, a tert-amyl group, etc. Above all, preferred are a hydrogen atom and an alkyl group having from 1 to 4 carbon atoms; more preferred are a hydrogen atom and a methyl group; and even more preferred is a hydrogen atom.

$X^1$ in the general formula (I) represents a group selected from —S(=O)—, —S(=O)$_2$—, —C(=O)—, —C(R$^3$R$^4$)—, —P(=O)(OR$^5$)— and —SiR$^6$R$^7$—, preferably a group selected from —S(=O)—, —C(=O)—, —CR$^3$R$^4$— and —P(=O)(OR$^5$)—, even more preferably —S(=O)— or —C(=O)—, still more preferably —S(=O)—.

In this, $R^3$ and $R^4$ each represent a hydrogen atom or an alkyl group having from 1 to 6 carbon atoms, preferably a hydrogen atom or an alkyl group having from 1 to 4 carbon atoms, more preferably a hydrogen atom, a methyl group or an ethyl group.

$R^5$ to $R^7$ each represent an alkyl group having from 1 to 6 carbon atoms, preferably an alkyl group having from 1 to 4 carbon atoms, more preferably a methyl group or an ethyl group.

The linear or branched alkylsulfanyl group having from 1 to 6 carbon atoms of $Y^1$ in the general formula (I) includes a methylsulfinyl group, an ethylsulfinyl group, a propylsulfinyl group, a butylsulfinyl group, a pentylsulfinyl group, a hexylsulfinyl group, a trifluoromethylsulfinyl group, a 2,2,2-trifluoroethylsulfinyl group, an isopropylsulfinyl group, a sec-butylsulfinyl group, a tert-butylsulfinyl group, a tert-amylsulfinyl group, etc. Above all, preferred are linear alkylsulfinyl groups such as a methylsulfinyl group, an ethylsulfinyl group, a propylsulfinyl group, a butylsulfinyl group, etc.; and more preferred are a methylsulfinyl group and an ethylsulfinyl group.

The linear or branched alkenylsulfinyl group having from 2 to 6 carbon atoms of $Y^1$ in the general formula (I) includes a vinylsulfinyl group, a 2-propenylsulfinyl group, a 2-butenylsulfinyl group, a 3-butenylsulfinyl group, a 4-pentenylsulfinyl group, a 2-methyl-2-propenylsulfinyl group, a 2-methyl-2-butenylsulfinyl group, a 3-methyl-2-butenylsulfinyl group, etc. Above all, preferred are linear alkenylsulfinyl groups such as a vinylsulfinyl group, a 2-propenylsulfinyl group, a 2-butenylsulfinyl group, a 3-butenylsulfinyl group, etc.; and more preferred are a vinylsulfinyl group and a 2-propenylsulfinyl group.

The linear or branched alkynylsulfinyl group having from 3 to 6 carbon atoms of $Y^1$ in the general formula (I) includes a 2-propynylsulfinyl group, a 2-butynylsulfinyl group, a 3-butynylsulfinyl group, a 4-pentynylsulfinyl group, a 1-methyl-2-propynylsulfinyl group, a 1-methyl-2-butynylsulfinyl group, a 1,1-dimethyl-2-propynylsulfinyl group, etc. Above all, preferred are a 2-propynylsulfinyl group, a 2-butynylsulfinyl group, a 3-butynylsulfinyl group, and a 1-methyl-2-propynylsulfinyl group; and more preferred are a 2-propynylsulfinyl group, and a 1-methyl-2-propynylsulfinyl group.

The arylsulfinyl group having from 6 to 12 carbon atoms of $Y^1$ in the general formula (I) includes a phenylsulfinyl group, a benzylsulfinyl group, a tolylsulfinyl group, etc. Above all, preferred are a phenylsulfinyl group, and a benzylsulfinyl group; and more preferred is a phenylsulfinyl group.

The linear or branched alkylsulfonyl group having from 1 to 6 carbon atoms of $Y^1$ in the general formula (I) includes a methylsulfonyl group, an ethylsulfonyl group, a propylsulfonyl group, a butylsulfonyl group, a pentylsulfonyl group, a hexylsulfonyl group, a trifluoromethylsulfonyl group, a 2,2,2-trifluoroethylsulfonyl group, a 2-propylsulfonyl group, a sec-butylsulfonyl group, a 1,1-dimethylethylsulfonyl group, a 1,1-dimethylpentylsulfonyl group, etc. Above all, preferred are linear alkylsulfonyl groups such as a methylsulfonyl group, an ethylsulfonyl group, a propylsulfonyl group, a butylsulfonyl group, etc.; and more preferred are a methylsulfonyl group and an ethylsulfonyl group.

The linear or branched alkenylsulfonyl group having from 2 to 6 carbon atoms of $Y^1$ in the general formula (I) includes a vinylsulfonyl group, a 2-propenylsulfonyl group, a 2-butenylsulfonyl group, a 3-butenylsulfonyl group, a 4-pentenylsulfonyl group, a 2-methyl-2-propenylsulfonyl group, a 2-methyl-2-butenylsulfonyl group, a 3-methyl-2-butenylsulfonyl group, etc. Above all, preferred are linear alkenylsulfonyl groups such as a vinylsulfonyl group, a 2-propenylsulfonyl group, a 2-butenylsulfonyl group, a 3-butenylsulfonyl group, etc.; and more preferred are a vinylsulfonyl group, and a 2-propenylsulfonyl group.

The linear or branched alkynylsulfonyl group having from 3 to 6 carbon atoms of $Y^1$ in the general formula (I) includes a 2-propynylsulfonyl group, a 2-butynylsulfonyl group, a 3-butynylsulfonyl group, a 4-pentynylsulfonyl group, a 1-methyl-2-propynylsulfonyl group, a 1-methyl-2-butynylsulfonyl group, a 1,1-dimethyl-2-propynylsulfonyl group, etc. Above all, preferred are 2-propynylsulfonyl group, a 2-butynylsulfonyl group, a 3-butynylsulfonyl group, and a 1-methyl-2-propynylsulfonyl group; and more preferred are a 2-propynylsulfonyl group, and a 1-methyl-2-propynylsulfonyl group.

The arylsulfonyl group having from 6 to 12 carbon atoms of $Y^1$ in the general formula (I) includes a phenylsulfonyl group, a benzylsulfonyl group, a tolylsulfonyl group, etc. Above all, preferred are a phenylsulfonyl group and a benzylsulfonyl group; and more preferred is a phenylsulfonyl group.

Of the above-mentioned substituents, $Y^1$ in the general formula (I) is more preferably a methylsulfinyl group, an ethylsulfinyl group, a vinylsulfinyl group, a 2-propenylsulfinyl group, a methylsulfonyl group, an ethylsulfonyl group, a vinylsulfonyl group, a 2-propenylsulfonyl group, or a 2-propynylsulfonyl group, and even more preferably one having a sulfonyl group, such as a methylsulfonyl group, an ethylsulfonyl group, a vinylsulfonyl group, etc.

$Z^1$ in the general formula (I) represents a hydrogen atom, an alkyl group having from 1 to 4 carbon atoms, an alkylsulfinylmethyl group having from 2 to 7 carbon atoms, an alkenylsulfinylmethyl group having from 3 to 7 carbon atoms, an alkynylsulfinylmethyl group having from 4 to 7 carbon atoms, an arylsulfinylmethyl group having from 7 to 13 carbon atoms, an alkylsulfonylmethyl group having from 2 to 7 carbon atoms, an alkenylsulfonylmethyl group having from 3 to 7 carbon atoms, an alkynylsulfonylmethyl group having from 4 to 7 carbon atoms, or an arylsulfonylmethyl group having from 7 to 13 carbon atoms.

$Z^1$ in the general formula (I) representing a hydrogen atom or an alkyl group having from 1 to 4 carbon atoms is preferably a hydrogen atom, a methyl group or an ethyl group, and is more preferably a hydrogen atom.

In case where $Z^1$ is a linear or branched alkyl group having from 1 to 4 carbon atoms, $Z^1$ may bond to $Y^1$ to form a ring, but more preferably does not form a ring.

The linear or branched alkylsulfinylmethyl group having from 2 to 7 carbon atoms of $Z^1$ in the general formula (I) includes a methylsulfinylmethyl group, an ethylsulfinylmethyl group, a propylsulfinylmethyl group, a butylsulfinylmethyl group, a pentylsulfinylmethyl group, a hexylsulfinylmethyl group, a trifloromethylsulfinylmethyl group, a 2,2,2-trifluoroethylsulfinylmethyl group, a 2-propylsulfinylmethyl group, a sec-butylsulfinylmethyl group, a 1,1-dimethylethylsulfinylmethyl group, a 1,1-dimethylpentylsulfinylmethyl group, etc. Above all, preferred are a methylsulfinylmethyl group, an ethylsulfinylmethyl group, a propylsulfinylmethyl group, and a butylsulfinylmethyl group; and more preferred are a methylsulfinylmethyl group and an ethylsulfinylmethyl group.

The linear or branched alkenylsulfinylmethyl group having from 3 to 7 carbon atoms of $Z^1$ in the general formula (I) includes a vinylsulfinylmethyl group, a 2-propenylsulfinylmethyl group, a 2-butenylsulfinylmethyl group, a 3-butenylsulfinylmethyl group, a 4-pentenylsulfinylmethyl group, a 2-methyl-2-propenylsulfinylmethyl group, a 2-methyl-2-butenylsulfinylmethyl group, a 3-methyl-2-butenylsulfinylmethyl group, etc. Above all, preferred are a vinylsulfinylmethyl group, a 2-propenylsulfinylmethyl group, a 2-butenylsulfinylmethyl group, and a 3-butenylsulfinylmethyl group; and more preferred are a vinylsulfinylmethyl group, and a 2-propenylsulfinylmethyl group.

The linear or branched alkynylsulfinylmethyl group having from 4 to 7 carbon atoms of $Z^1$ in the general formula (I) includes a 2-propynylsulfinylmethyl group, a 2-butynylsulfinylmethyl group, a 3-butynylsulfinylmethyl group, a 4-pentynylsulfinylmethyl group, a 1-methyl-2-propynylsulfinylmethyl group, a 1-methyl-2-butynylsulfinylmethyl group, a 1,1-dimethyl-2-propynylsulfinylmethyl group, etc. Above all, preferred are 2-propynylsulfinylmethyl group, a 2-butynylsulfinylmethyl group, a 3-butynylsulfinylmethyl group, and a 1-methyl-2-propynylsulfinylmethyl group; and more preferred are a 2-propynylsulfinylmethyl group, and a 1-methyl-2-propynylsulfinylmethyl group.

The arylsulfinylmethyl group having from 7 to 13 carbon atoms of $Z^1$ in the general formula (I) includes a phenylsulfinylmethyl group, a benzylsulfinylmethyl group, a tolylsulfinylmethyl group, etc. Above all, preferred are a phenylsulfinylmethyl group, and a benzylsulfinylmethyl group; and more preferred is a phenylsulfinylmethyl group.

The linear or branched alkylsulfonylmethyl group having from 2 to 7 carbon atoms of $Z^1$ in the general formula (I) includes a methylsulfonylmethyl group, an ethylsulfonylmethyl group, a propylsulfonylmethyl group, a butylsulfonylmethyl group, a pentylsulfonylmethyl group, a hexylsulfonylmethyl group, a trifluoromethylsulfonylmethyl group, a 2,2,2-trifluoroethylsulfonylmethyl group, a 2-propylsulfonylmethyl group, a sec-butylsulfonylmethyl group, a 1,1-dimethylethylslfonylmethyl group, a 1,1-dimethylpentanesulfonylmethyl group, etc. Above all, preferred are a methylsulfonylmethyl group, an ethylsulfonylmethyl group, a propylsulfonylmethyl group, and a butylsulfonylmethyl group; and more preferred are a methylsulfonylmethyl group, and an ethylsulfonylmethyl group.

The linear or branched alkenylsulfonylmethyl group having from 3 to 7 carbon atoms of $Z^1$ in the general formula (I) includes a vinylsulfonylmethyl group, a 2-propenylsulfonylmethyl group, a 2-butenylsulfonylmethyl group, a 3-butenylsulfonylmethyl group, a 4-pentenylsulfonylmethyl group, a 2-methyl-2-propenylsulfonylmethyl group, a 2-methyl-2-butenylsulfonylmethyl group, a 3-methyl-2-butenylsulfonylmethyl group, etc. Above all, preferred are a vinylsulfonylmethyl group, a 2-propenylsulfonylmethyl group, a 2-butenylsulfonylmethyl group, and a 3-butenylsulfonylmethyl group; and more preferred are a vinylsulfonylmethyl group, and a 2-propenylsulfonylmethyl group.

The linear or branched alkynylsulfonylmethyl group having from 4 to 7 carbon atoms of $Z^1$ in the general formula (I) includes a 2-propynylsulfonylmethyl group, a 2-butynylsulfonylmethyl group, a 3-butynylsulfonylmethyl group, a 4-pentynylsulfonylmethyl group, a 1-methyl-2-propynylsulfonylmethyl group, a 1-methyl-2-butynylsulfonylmethyl group, a 1,1-dimethyl-2-propynylsulfonylmethyl group, etc. Above all, preferred are a 2-propynylsulfonylmethyl group, a 2-butynylsulfonylmethyl group, a 3-butynylsulfonylmethyl group, and a 1-methyl-2-propynylsulfonylmethyl group; and more preferred are a 2-propynylsulfonylmethyl group, and a 1-methyl-2-propynylsulfonylmethyl group.

The arylsulfonylmethyl group having from 7 to 13 carbon atoms of $Z^1$ in the general formula (I) includes a phenylsulfonylmethyl group, a benzylsulfonylmethyl group, a tolylsulfonylmethyl group, etc. Above all, preferred are a phenylsulfonylmethyl group, and a benzylsulfonylmethyl group; and more preferred is a phenylsulfonylmethyl group.

Of the above-mentioned substituents, $Z^1$ in the general formula (I) is more preferably a hydrogen atom, a methyl group, a methylsulfinylmethyl group, an ethylsulfinylmethyl group, a vinylsulfinylmethyl group, a 2-propenylsulfinylmethyl group, a methylsulfonylmethyl group, an ethylsulfonylmethyl group, a vinylsulfonylmethyl group, a 2-propenylsulfonylmethyl group, or a 2-propynylsulfonylmethyl group, even more preferably a hydrogen atom, a methyl group, a methylsulfonylmethyl group, an ethylsulfonylmethyl group, or a vinylsulfonylmethyl group, still more preferably a hydrogen atom, a methylsulfonylmethyl group, an ethylsulfonylmethyl group, or a vinylsulfonylmethyl group, and furthermore preferably a hydrogen atom.

The halogen atom with which the hydrogen atom on the carbon atom of $X^1$, $Y^1$ and $Z^1$ is substituted includes a fluorine atom, a chlorine atom, a bromine atom, and an iodine atom, but is preferably a fluorine atom or a chlorine atom, more preferably a fluorine atom.

The compounds where $X^1$, $Y^1$ and $Z^1$ each are the above-mentioned substituent are preferred as markedly improving low-temperature load characteristics after high-temperature charging storage.

Specific examples of the 1,2-dioxypropane compounds represented by the general formula (I) include the following:
(1) As the case where $X^1$ is —S(=O)—:
Preferably mentioned are 4-(methylsulfinylmethyl)-1,3,2-dioxathiolane-2-oxide, 4-(ethylsulfinylmethyl)-1,3,2-dioxathiolane-2-oxide, 4-(vinylsulfinylmethyl)-1,3,2-dioxathiolane-2-oxide, 4-(2-propenylsulfinylmethyl)-1,3,2-dioxathiolane-2-oxide, 4-(2-propynylsulfinylmethyl)-1,3,2-dioxathiolane-2-oxide, 4-(trifluoromethylsulfinylmethyl)-1,3,2-dioxathiolane-2-oxide, 4-(phenylsulfinylmethyl)-1,3,2-dioxathiolane-2-oxide, 4-(methylsulfonylmethyl)-1,3,2-dioxathiolane-2-oxide, 4-(ethylsulfonylmethyl)-1,3,2-dioxathiolane-2-oxide, 4-(vinylsulfonylmethyl)-1,3,2-dioxathiolane-2-oxide, 4-(2-propenylsulfonylmethyl)-1,3,2-dioxathiolane-2-oxide, 4-(2-propynylsulfonylmethyl)-1,3,2-dioxathiolane-2-oxide, 4-(trifluoromethylsulfonylmethyl)-1,3,2-dioxathiolane-2-oxide, 4-(phenylsulfonylmethyl)-1,3,2-dioxathiolane-2-oxide, 4,5-bis(methylsulfinylmethyl)-1,3,2-dioxathiolane-2-oxide, 4,5-bis(ethylsulfinylmethyl)-1,3,2-dioxathiolane-2-oxide, 4,5-bis(vinylsulfinylmethyl)-1,3,2-dioxathiolane-2-oxide, 4,5-bis(2-propenylsulfinylmethyl)-1,3,2-dioxathiolane-2-oxide, 4,5-bis(2-propynylsulfinylmethyl)-1,3,2-dioxathiolane-2-oxide, 4,5-bis(phenylsulfinylmethyl)-1,3,2-dioxathiolane-2-oxide, 4,5-bis(methylsulfonylmethyl)-1,3,2-dioxathiolane-2-oxide, 4,5-bis(ethylsulfonylmethyl)-1,3,2-dioxathiolane-2-oxide, 4,5-bis(vinylsulfonylmethyl)-1,3,2-dioxathiolane-2-oxide, 4,5-bis(2-propenylsulfonylmethyl)-1,3,2-dioxathiolane-2-oxide, 4,5-bis(2-propynylsulfonylmethyl)-1,3,2-dioxathiolane-2-oxide, and 4,5-bis(phenylsulfonylmethyl)-1,3,2-dioxathiolane-2-oxide.

As the compounds where $Y^1$ and $Z^1$ bond to each other to form a ring, preferably mentioned are tetrahydro-thieno[3,4-d]-1,3,2-dioxathiolane-2,5-dioxide, tetrahydro-thieno[3,4-d]-1,3,2-dioxathiolane-2,5,5-trioxide, etc.

(2) As the case where $X^1$ is —S(=O)$_2$—:
Preferably mentioned are 4-(methylsulfinylmethyl)-1,3,2-dioxathiolane-2,2-dioxide, 4-(ethylsulfinylmethyl)-1,3,2-dioxathiolane-2,2-dioxide, 4-(vinylsulfinylmethyl)-1,3,2-dioxathiolane-2,2-dioxide, 4-(2-propenylsulfinylmethyl)-1,3,2-dioxathiolane-2,2-dioxide, 4-(2-propynylsulfinylmethyl)-1,3,2-dioxathiolane-2,2-dioxide, 4-(trifluoromethylsulfinylmethyl)-1,3,2-dioxathiolane-2,2-dioxide, 4-(phenylsulfinylmethyl)-1,3,2-dioxathiolane-2,2-dioxide, 4-(methylsulfonylmethyl)-1,3,2-dioxathiolane-2,2-dioxide, 4-(ethylsulfonylmethyl)-1,3,2-dioxathiolane-2,2-dioxide, 4-(vinylsulfonylmethyl)-1,3,2-dioxathiolane-2,2-dioxide, 4-(2-propenylsulfonylmethyl)-1,3,2-dioxathiolane-2,2-dioxide, 4-(2-propynylsulfonylmethyl)-1,3,2-dioxathiolane-2,2-dioxide, 4-(trifluoromethylsulfonylmethyl)-1,3,2-dioxathiolane-2,2-dioxide, 4-(phenylsulfonylmethyl)-1,3,2-dioxathiolane-2,2-dioxide, 4,5-bis(methylsulfinylmethyl)-1,3,2-dioxathiolane-2,2-dioxide, 4,5-bis(ethylsulfinylmethyl)-1,3,2-dioxathiolane-2,2-dioxide, 4,5-bis(vinylsulfinylmethyl)-1,3,2-dioxathiolane-2,2-dioxide, 4,5-bis(2-propenylsulfinylmethyl)-1,3,2-dioxathiolane-2,2-dioxide, 4,5-bis(2-propynylsulfinylmethyl)-1,3,2-dioxathiolane-2,2-dioxide, 4,5-bis(phenylsulfinylmethyl)-1,3,2-dioxathiolane-2,2-dioxide, 4,5-bis(methylsulfonylmethyl)-1,3,2-dioxathiolane-2,2-dioxide, 4,5-bis(ethylsulfonylmethyl)-1,3,2-dioxathiolane-2,2-dioxide, 4,5-bis(vinylsulfonylmethyl)-1,3,2-dioxathiolane-2,2-dioxide, 4,5-bis(2-propenylsulfonylmethyl)-1,3,2-dioxathiolane-2,2-dioxide, 4,5-bis(2-propynylsulfonylmethyl)-1,3,2-dioxathiolane-2,2-dioxide, and 4,5-bis(phenylsulfonylmethyl)-1,3,2-dioxathiolane-2,2-dioxide.

As the compounds where $Y^1$ and $Z^1$ bond to each other to form a ring, preferably mentioned are tetrahydro-thieno[3,4-d]-1,3,2-dioxathiolane-2,2,5-trioxide, tetrahydro-thieno[3,4-d]-1,3,2-dioxathiolane-2,2,5,5-tetraoxide, etc.

(3) As the case where $X^1$ is —C(=O)—:
Preferably mentioned are 4-(methylsulfinylmethyl)-1,3-dioxathiolan-2-one, 4-(ethylsulfinylmethyl)-1,3-dioxathiolan-2-one, 4-(vinylsulfinylmethyl)-1,3-dioxathiolan-2-one, 4-(2-propenylsulfinylmethyl)-1,3-dioxathiolan-2-one, 4-(2-propynylsulfinylmethyl)-1,3-dioxathiolan-2-one, 4-(trifluoromethylsulfinylmethyl)-1,3-dioxathiolan-2-one, 4-(phenylsulfinylmethyl)-1,3-dioxathiolan-2-one, 4-(methylsulfonylmethyl)-1,3-dioxathiolan-2-one, 4-(ethylsulfonylmethyl)-1,3-dioxathiolan-2-one, 4-(vinylsulfonylmethyl)-1,3-dioxathiolan-2-one, 4-(2-propenylsulfonylmethyl)-1,3-dioxathiolan-2-one, 4-(2-propynylsulfonylmethyl)-1,3-dioxathiolan-2-one, 4-(trifluoromethylsulfonylmethyl)-1,3-dioxathiolan-2-one, 4-(phenylsulfonylmethyl)-1,3-dioxathiolan-2-one, 4,5-bis(methylsulfinylmethyl)-1,3-dioxathiolan-2-one, 4,5-bis(ethylsulfinylmethyl)-1,3-dioxathiolan-2-one, 4,5-bis(vinylsulfinylmethyl)-1,3-dioxathiolan-2-one, 4,5-bis(2-propenylsulfinylmethyl)-1,3-dioxathiolan-2-one, 4,5-bis(2-propynylsulfinylmethyl)-1,3-dioxathiolan-2-one, 4,5-bis(phenylsulfinylmethyl)-1,3-dioxathiolan-2-one, 4,5-bis(methylsulfonylmethyl)-1,3-dioxathiolan-2-one, 4,5-bis(ethylsulfonylmethyl)-1,3-dioxathiolan-2-one, 4,5-bis(vinylsulfonylmethyl)-1,3-dioxathiolan-2-one, 4,5-bis(2-propenylsulfonylmethyl)-1,3-dioxathiolan-2-one, 4,5-bis(2-propynylsulfonylmethyl)-1,3-dioxathiolan-2-one, and 4,5-bis(phenylsulfonylmethyl)-1,3-dioxathiolan-2-one.

As the compounds where $Y^1$ and $Z^1$ bond to each other to form a ring, preferably mentioned are tetrahydro-thieno[3,4-d]-1,3-dioxole-2,5-dioxide, tetrahydro-thieno[3,4-d]-1,3-dioxole-2,5,5-trioxide, etc.

(4) As the case where $X^1$ is —$CR^3R^4$—:

Preferably mentioned are 4-(methylsulfinylmethyl)-1,3-dioxolane, 4-(ethylsulfinylmethyl)-1,3-dioxolane, 4-(vinylsulfinylmethyl)-1,3-dioxolane, 4-(2-propenylsulfinylmethyl)-1,3-dioxolane, 4-(2-propynylsulfinylmethyl)-1,3-dioxolane, 4-(trifluoromethylsulfinylmethyl)-1,3-dioxolane, 4-(phenylsulfinylmethyl)-1,3-dioxolane, 4-(methylsulfonylmethyl)-1,3-dioxolane, 4-(ethylsulfonylmethyl)-1,3-dioxolane, 4-(vinylsulfonylmethyl)-1,3-dioxolane, 4-(2-propenylsulfonylmethyl)-1,3-dioxolane, 4-(2-propynylsulfonylmethyl)-1,3-dioxolane, 4-(trifluoromethylsulfonylmethyl)-1,3-dioxolane, 4-(phenylsulfonylmethyl)-1,3-dioxolane, 4,5-bis(methylsulfinylmethyl)-1,3-dioxolane, 4,5-bis(ethylsulfinylmethyl)-1,3-dioxolane, 4,5-bis(vinylsulfinylmethyl)-1,3-dioxolane, 4,5-bis(2-propenylsulfinylmethyl)-1,3-dioxolane, 4,5-bis(2-propynylsulfinylmethyl)-1,3-dioxolane, 4,5-bis(phenylsulfinylmethyl)-1,3-dioxolane, 4,5-bis(methylsulfonylmethyl)-1,3-dioxolane, 4,5-bis(ethylsulfonylmethyl)-1,3-dioxolane, 4,5-bis(vinylsulfonylmethyl)-1,3-dioxolane, 4,5-bis(2-propenylsulfonylmethyl)-1,3-dioxolane, 4,5-bis(2-propynylsulfonylmethyl)-1,3-dioxolane, and 4,5-bis(phenylsulfonylmethyl)-1,3-dioxolane.

As the compounds where $Y^1$ and $Z^1$ bond to each other to form a ring, preferably mentioned are 2,2-dimethyl-tetrahydro-thieno[3,4-d]-1,3-dioxole-5-oxide, 2,2-dimethyl-tetrahydro-thieno[3,4-d]-1,3-dioxole-5,5-dioxide, etc.

(5) As the case where $X^1$ is —$P(=O)(OR^5)$—:

Preferably mentioned are 2-methoxy-4-(methylsulfinylmethyl)-1,3,2-dioxaphospholane-2-oxide, 2-methoxy-4-(ethylsulfinylmethyl)-1,3,2-dioxaphospholane-2-oxide, 2-methoxy-4-(vinylsulfinylmethyl)-1,3,2-dioxaphospholane-2-oxide, 2-methoxy-4-(2-propenylsulfinylmethyl)-1,3,2-dioxaphospholane-2-oxide, 2-methoxy-4-(2-propynylsulfinylmethyl)-1,3,2-dioxaphospholane-2-oxide, 2-methoxy-4-(trifluoromethylsulfinylmethyl)-1,3,2-dioxaphospholane-2-oxide, 2-methoxy-4-(phenylsulfinylmethyl)-1,3,2-dioxaphospholane-2-oxide, 2-methoxy-4-(methylsulfonylmethyl)-1,3,2-dioxaphospholane-2-oxide, 2-methoxy-4-(ethylsulfonylmethyl)-1,3,2-dioxaphospholane-2-oxide, 2-methoxy-4-(vinylsulfonylmethyl)-1,3,2-dioxaphospholane-2-oxide, 2-methoxy-4-(2-propenylsulfonylmethyl)-1,3,2-dioxaphospholane-2-oxide, 2-methoxy-4-(2-propynylsulfonylmethyl)-1,3,2-dioxaphospholane-2-oxide, 2-methoxy-4-(trifluoromethylsulfonylmethyl)-1,3,2-dioxaphospholane-2-oxide, 2-methoxy-4-(phenylsulfonylmethyl)-1,3,2-dioxaphospholane-2-oxide, 4,5-bis(methylsulfinylmethyl)-2-methoxy-1,3,2-dioxaphospholane-2-oxide, 4,5-bis(ethylsulfinylmethyl)-2-methoxy-1,3,2-dioxaphospholane-2-oxide, 4,5-bis(vinylsulfinylmethyl)-2-methoxy-1,3,2-dioxaphospholane-2-oxide, 4,5-bis(2-propenylsulfinylmethyl)-2-methoxy-1,3,2-dioxaphospholane-2-oxide, 4,5-bis(2-propynylsulfinylmethyl)-2-methoxy-1,3,2-dioxaphospholane-2-oxide, 4,5-bis(phenylsulfinylmethyl)-2-methoxy-1,3,2-dioxaphospholane-2-oxide, 4,5-bis(methylsulfonylmethyl)-2-methoxy-1,3,2-dioxaphospholane-2-oxide, 4,5-bis(ethylsulfonylmethyl)-2-methoxy-1,3,2-dioxaphospholane-2-oxide, 4,5-bis(vinylsulfonylmethyl)-2-methoxy-1,3,2-dioxaphospholane-2-oxide, 4,5-bis(2-propenylsulfonylmethyl)-2-methoxy-1,3,2-dioxaphospholane-2-oxide, 4,5-bis(2-propynylsulfonylmethyl)-2-methoxy-1,3,2-dioxaphospholane-2-oxide, and 4,5-bis(phenylsulfonylmethyl)-2-methoxy-1,3,2-dioxaphospholane-2-oxide.

As the compounds where $Y^1$ and $Z^1$ bond to each other to form a ring, preferably mentioned are 2-methoxy-tetrahydro-thieno[3,4-d]-1,3,2-dioxaphospholane-2,2-dioxide, and 2-methoxy-tetrahydro-thieno[3,4-d]-1,3,2-dioxaphospholane-2,2,2-trioxide.

(6) As the case where $X^1$ is —$SiR^6R^7$—:

Preferably mentioned are 2,2-dimethyl-4-(methylsulfinylmethyl)-1,3,2-dioxasilolane, 2,2-dimethyl-4-(ethylsulfinylmethyl)-1,3,2-dioxasilolane, 2,2-dimethyl-4-(vinylsulfinylmethyl)-1,3,2-dioxasilolane, 2,2-dimethyl-4-(2-propenylsulfinylmethyl)-1,3,2-dioxasilolane, 2,2-dimethyl-4-(2-propynylsulfinylmethyl)-1,3,2-dioxasilolane, 2,2-dimethyl-4-(trifluoromethylsulfinylmethyl)-1,3,2-dioxasilolane, 2,2-dimethyl-4-(phenylsulfinylmethyl)-1,3,2-dioxasilolane, 2,2-dimethyl-4-(methylsulfonylmethyl)-1,3,2-dioxasilolane, 2,2-dimethyl-4-(ethylsulfonylmethyl)-1,3,2-dioxasilolane, 2,2-dimethyl-4-(vinylsulfonylmethyl)-1,3,2-dioxasilolane, 2,2-dimethyl-4-(2-propenylsulfonylmethyl)-1,3,2-dioxasilolane, 2,2-dimethyl-4-(2-propynylsulfonylmethyl)-1,3,2-dioxasilolane, 2,2-dimethyl-4-(trifluoromethylsulfonylmethyl)-1,3,2-dioxasilolane, 2,2-dimethyl-4-(phenylsulfonylmethyl)-1,3,2-dioxasilolane, 4,4-bis(methylsulfinylmethyl)-2,2-dimethyl-1,3,2-dioxasilolane, 4,4-bis(ethylsulfinylmethyl)-2,2-dimethyl-1,3,2-dioxasilolane, 4,4-bis(vinylsulfinylmethyl)-2,2-dimethyl-1,3,2-dioxasilolane, 4,4-bis(2-propenylsulfinylmethyl)-2,2-dimethyl-1,3,2-dioxasilolane, 4,4-bis(2-propynylsulfinylmethyl)-2,2-dimethyl-1,3,2-dioxasilolane, 4,4-bis(trifluoromethylsulfinylmethyl)-2,2-dimethyl-1,3,2-dioxasilolane, 4,4-bis(phenylsulfinylmethyl)-2,2-dimethyl-1,3,2-dioxasilolane, 4,4-bis(methylsulfonylmethyl)-2,2-dimethyl-1,3,2-dioxasilolane, 4,4-bis(ethylsulfonylmethyl)-2,2-dimethyl-1,3,2-dioxasilolane, 4,4-bis(vinylsulfonylmethyl)-2,2-dimethyl-1,3,2-dioxasilolane, 4,4-bis(2-propenylsulfonylmethyl)-2,2-dimethyl-1,3,2-dioxasilolane, 4,4-bis(2-propynylsulfonylmethyl)-2,2-dimethyl-1,3,2-dioxasilolane, 4,4-bis(trifluoromethylsulfonylmethyl)-2,2-dimethyl-1,3,2-dioxasilolane, and 4,4-bis(phenylsulfonylmethyl)-2,2-dimethyl-1,3,2-dioxasilolane.

As the compounds where $Y^1$ and $Z^1$ bond to each other to form a ring, preferably mentioned are 2,2-dimethyl-tetrahydro-thieno[3,4-d]-1,3,2-dioxasilolane-5-oxide, and 2,2-dimethyl-tetrahydro-thieno[3,4-d]-1,3,2-dioxasilolane-5,5-dioxide.

From the viewpoint of improving low-temperature load characteristics after high-temperature charging storage, the following are more preferred from among the above-mentioned compounds: 4-(methylsulfonylmethyl)-1,3,2-dioxathiolane-2-oxide, 4-(vinylsulfonylmethyl)-1,3,2-dioxathiolane-2-oxide, 4-(2-propynylsulfonylmethyl)-1,3,2-dioxathiolane-2-oxide, 4,5-bis(methylsulfonylmethyl)-1,3,2-dioxathiolane-2-oxide, 4-(methylsulfonylmethyl)-1,3-dioxolan-2-one, 4-(2-propynylsulfonylmethyl)-1,3-dioxolan-2-one, 4-(methylsulfonylmethyl)-1,3-dioxolane, tetrahydro-thieno[3,4-d]-1,3,2-dioxathiolane-2,5,5-trioxide, 4,5-bis(methylsulfonylmethyl)-1,3-dioxolan-2-one, 4-(vinylsulfonylmethyl)-1,3,2-dioxathiolane-2-oxide, 2-methoxy-4-(methylsulfonylmethyl)-1,3,2-dioxaphospholane-2-oxide, 4-(methylsulfonylmethyl)-1,3,2-dioxathiolane-2,2-dioxide, and 2,2-dimethyl-4-(methylsulfonylmethyl)-1,3,2-dioxasilolane. Even more preferred are 4-(methylsulfonylmethyl)-1,3,2-dioxathiolane-2-oxide, 4-(methylsulfonylmethyl)-1,3-dioxolan-2-one, 4-(methylsulfonylmethyl)-1,3-dioxolane, tetrahydro-thieno[3,4-d]-1,3,2-dioxathiolane-2,5,5-trioxide, 4-(vinylsulfonylmethyl)-1,3,2-dioxathiolane-2-oxide, 2-methoxy-4-(methylsulfonylmethyl)-1,3,2-dioxaphospholane-2-oxide, 4-(methylsulfonylmethyl)-1,3,2-dioxathiolane-2,2-dioxide, and 2,2-dimethyl-4-(methylsulfonylmethyl)-1,3,2-dioxasilolane.

The 1,2-dioxypropane compound represented by the general formula (I) includes optical isomers. The optical isomers include R-form and S-form, both of which exhibit the effect of the present invention. The optical isomers may be in the form of a mixture thereof in a desired ratio; and both a case where one optical isomer is excessive over the other (optical active form) and a case where the two optical isomers exist in the same amount (racemic form) exhibit the effect of the present invention.

Further, in the general formula (I) where $X^1$ is a group $>S=O$, $Y^1$ is a sulfinyl group, or $Z^1$ is a group except hydrogen, the formula may have two asymmetric centers, and consequently, the formula may further include diastereomers in addition to the above-mentioned optical isomers. The diastereomers are not always the same in point of the chemical property or the electrochemical property thereof; and therefore, depending on the ratio of the diastereomers, the degree of the effect of the present invention may vary; however, any case where any of the optical isomers is used either singly or in the form of a mixture thereof can exhibit the effect of the present invention.

The content of the 1,2-dioxypropane compound represented by the general formula (I) to be contained in the nonaqueous electrolytic solution of the present invention is preferably from 0.001 to 20% by mass of the nonaqueous electrolytic solution. When the content is at most 20% by mass, then the risk of excessive formation of a surface film on the electrode to worsen the low-temperature load characteristics after high-temperature charging storage could be low; and when at least 0.001% by mass, then the surface film formation would be sufficient and the effect of improving low-temperature load characteristics after high-temperature charging storage could be enhanced. The content is preferably at least 0.01% by mass of the nonaqueous electrolytic solution, more preferably at least 0.05% by mass, even more preferably at least 0.3% by mass, and its upper limit is preferably at most 10% by mass, more preferably at most 5% by mass, even more preferably at most 3% by mass.

When added to the nonaqueous electrolytic solution of the present invention, the 1,2-dioxypropane compound represented by the general formula (I) can improve low-temperature load characteristics after high-temperature charging storage; but when combined with a nonaqueous solvent, an electrolyte salt and further other additives to be mentioned below, the compound can exhibit a specific effect of synergistically improving low-temperature load characteristics after high-temperature charging storage. Though the reason is not clear, it may be considered that a mixture surface film having a high ionic conductivity and comprising the constitutive elements of the nonaqueous solvent, the electrolyte salt and the other additives could be formed.

[Nonaqueous Solvent]

The nonaqueous solvent for use in the nonaqueous electrolytic solution of the present invention includes cyclic carbonates, linear carbonates, linear esters, lactones, ethers, amides, phosphates, sulfones, nitriles, $S=O$ bond-containing compounds, etc.

The cyclic carbonates include ethylene carbonate (EC), propylene carbonate (PC), 1,2-butylene carbonate, 2,3-butylene carbonate, 4-fluoro-1,3-dioxolan-2-one (FEC), trans or cis-4,5-difluoro-1,3-dioxolan-2-one (hereinafter the two are collectively called "DFEC"), vinylene carbonate (VC), vinylethylene carbonate (VEC), etc.

Of those, preferred is use of at least one cyclic carbonate having a carbon-carbon double bond or a fluorine atom, as markedly enhancing the effect of improving low-temperature load characteristics after high-temperature charging storage; and more preferred is use of both a cyclic carbonate having a carbon-carbon double bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the carbon-carbon double bond-containing cyclic carbonate is preferably at least 0.07% by volume relative to the total volume of the nonaqueous solvent, more preferably at least 0.2% by volume, even more preferably at least 0.7% by volume, and the upper limit thereof is preferably at most 7% by volume, more preferably at most 4% by volume, even more preferably at most 2.5% by volume. Falling within the range, the cyclic carbonate can favorably form a surface film on an electrode, as combined with the 1,2-dioxypropane compound having a sulfinyl group or a sulfonyl group at the 3-position and represented by the general formula (I), and the stability of the surface film during high-temperature charging storage can be markedly enhanced not detracting from low-temperature load characteristics.

The content of the fluorine atom-containing cyclic carbonate is preferably at least 0.07% by volume relative to the total volume of the nonaqueous solvent, more preferably at least 4% by volume, even more preferably at least 7% by volume, and the upper limit thereof is preferably at most 35% by volume, more preferably at most 25% by volume, even more preferably at most 15% by volume. Falling within the range, the cyclic carbonate can favorably form a surface film on an electrode, as combined with the 1,2-dioxypropane compound having a sulfinyl group or a sulfonyl group at the 3-position and represented by the general formula (I), and the stability of the surface film during high-temperature charging storage can be markedly enhanced not detracting from low-temperature load characteristics.

In case where the nonaqueous solvent contains both the carbon-carbon double bond-containing cyclic carbonate and the fluorine atom-containing cyclic carbonate, the ratio of the carbon-carbon double bond-containing cyclic carbonate to the content of the fluorine atom-containing cyclic carbonate is preferably at least 0.2% by volume, more preferably at least 3% by volume, even more preferably at least 7% by volume, and its upper limit is preferably at most 40% by volume, more preferably at most 30% by volume, even more preferably at most 15% by volume. The range is especially preferred since the stability of the surface film during high-temperature charging storage can be further more markedly enhanced not detracting from low-temperature cycle characteristics.

Preferably, the nonaqueous solvent contains ethylene carbonate and/or propylene carbonate, as the resistance of the surface film formed on an electrode can be reduced. Preferably, the content of ethylene carbonate and/or propylene carbonate is at least 3% by volume relative to the total volume of the nonaqueous solvent, more preferably at least 5% by volume, even more preferably at least 7% by volume, and its upper limit is preferably at most 45% by volume, more preferably at most 35% by volume, even more preferably at most 25% by volume.

One kind of those solvents may be used, but using two or more different kinds as combined is preferred as further enhancing the effect of improving low-temperature cycle characteristics after high-temperature charging storage. Even more preferably, three or more different kinds are combined. Preferred combinations of the cyclic carbonates include EC and PC; EC and VC; PC and VC; VC and FEC; EC and FEC; PC and FEC; FEC and DFEC; EC and DFEC; PC and DFEC; VC and DFEC; VEC and DFEC; EC and PC and VC; EC and PC and FEC; EC and VC and FEC; EC and VC and VEC; PC and VC and FEC; EC and VC and DFEC; PC and VC and DFEC; EC and PC and VC and FEC; EC and PC and VC and DFEC; etc. Of those combinations, more preferred combinations are EC and VC; EC and FEC; PC and FEC; EC and PC and VC; EC and PC and FEC; EC and VC and FEC; PC and VC and FEC; EC and PC and VC and FEC; etc.

Not specifically defined, the content of the cyclic carbonate is preferably within a range of from 10 to 40% by volume relative to the total volume of the nonaqueous solvent. When the content is at least 10% by volume, then the risk of lowering the electric conductivity of the nonaqueous electrolytic solution to worsen low-temperature load characteristics after high-temperature charging storage may be low; and when the content is at most 40% by volume, then the risk of increasing the viscosity of the nonaqueous electrolytic solution to worsen low-temperature load characteristics after high-temperature charging storage may be low. Consequently, the content preferably falls within the above-mentioned range.

The linear carbonates include asymmetric linear carbonates such as methyl ethyl carbonate (MEC), methyl propyl carbonate (MPC), methyl isopropyl carbonate (MIPC), methyl butyl carbonate, ethyl propyl carbonate, etc.; symmetric linear carbonates such as dimethyl carbonate (DMC), diethyl carbonate (DEC), dipropyl carbonate, dibutyl carbonate, etc.

Above all, DMC and/or DEC are preferred as the symmetric linear carbonate, and DMC is more preferred. At least one of MEC, MPC and MIPC is preferred as the asymmetric linear carbonate, and MEC is most preferred. Further more preferred is combined use of an asymmetric linear carbonate and a symmetric linear carbonate. When combined, preferably, the ratio of the asymmetric linear carbonate in the linear carbonate is from 50 to 90% by volume.

Although one kind of those linear carbonates may be used, two or more kinds of them are preferably used in combination.

Using the linear carbonates as combined in the manner as above so as to have the composition falling within the above-mentioned range is preferred as enhancing the effect of improving low-temperature load characteristics after high-temperature charging storage.

Not specifically defined, the content of the linear carbonate is preferably within a range of from 60 to 90% by volume relative to the total volume of the nonaqueous solvent. When the content is at least 60% by volume, then the risk of increasing the viscosity of the nonaqueous electrolytic solution may be low; and when at most 90% by volume, then the risk of lowering the electric conductivity of the nonaqueous electrolytic solution may be low. Consequently, the above-mentioned range is preferred as bettering battery characteristics such as load characteristics, etc.

Regarding the ratio of the cyclic carbonate to the linear carbonate, the ratio of cyclic carbonate/linear carbonate (by volume) is preferably from 10/90 to 40/60, more preferably from 15/85 to 35/65, even more preferably from 20/80 to 30/70, from the viewpoint of improving low-temperature load characteristics after high-temperature charging storage.

The linear esters include methyl propionate, ethyl propionate, methyl acetate, ethyl acetate, methyl pivalate, butyl pivalate, hexyl pivalate, octyl pivalate, dimethyl oxalate, ethyl methyl oxalate, diethyl oxalate, etc. The lactones include γ-butyrolactone, γ-valerolactone, α-angelicalactone, etc.; the ethers include cyclic ethers such as tetrahydrofuran, 2-methyltetrahydrofuran, 1,3-dioxolane, 1,3-dioxane, 1,4-dioxane, etc.; and linear ethers such as 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the nitriles include acetonitrile, propionitrile, succinonitrile, glutaronitrile, adiponitrile, pimelonitrile, etc.

The S=O bond-containing compounds include sultone compounds such as 1,3-propanesultone, 1,3-butanesultone, 1,4-butanesultone, etc.; cyclic sulfite compounds such as ethylene sulfite, hexahydrobenzo[1,3,2]dioxathiol-2-oxide (also referred to as 1,2-cyclohexanediol cyclic sulfite), 5-vinylhexahydro-1,3,2-benzodioxathiol-2-oxide, etc.; sulfonic acid ester compounds such as 1,2-ethanediol dimethanesulfonate, 1,2-propanediol dimethanesulfonate, 1,3-propanediol dimethanesulfonate, 1,4-butanediol dimethanesulfonate, 1,5-pentanediol dimethanesulfonate, 2-propynyl methanesulfonate, methylenemethane disulfonate, etc.; and vinyl sulfone compounds such as divinyl sulfone, 1,2-bis(vinylsulfonyl)ethane, bis(2-vinylsulfonylethyl) ether, etc.

As other nonaqueous solvents, preferably used here are linear carboxylic acid anhydrides such as acetic anhydride, propionic anhydride, etc.; cyclic acid anhydrides such as succinic anhydride, maleic anhydride, glutaric anhydride, itaconic anhydride, 3-sulfo-propionic anhydride, etc.; cyclic phosphazene compounds such as methoxypentafluorocyclotriphosphazene, ethoxypentafluorocyclotriphosphazene, phenoxypentafluorocyclotriphosphazene, ethoxyheptafluorocyclotetraphosphazene, etc.; branched alkyl group-having aromatic compounds such as cyclohexylbenzene, fluorocyclohexylbenzene compounds (including 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc.; and other aromatic compounds such as biphenyl, terphenyls (o-, m-, and p-form), diphenyl ether, fluorobenzene, difluorobenzenes (o-, m-, and p-form), anisole, 2,4-difluoroanisole, partially hydrogenated terphenyls (including 1,2-dicyclohexylbenzene, 2-phenylbicyclohexyl, 1,2-diphenylcyclohexane, and o-cyclohexylbiphenyl), etc.

In general, the above-mentioned nonaqueous solvents are combined and used as a mixture thereof for attaining suitable physical properties. The combination includes, for example, a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, etc.

[Electrolyte Salt]

The electrolyte salt for use in the present invention includes lithium salts such as $LiPF_6$, $LiPO_2F_2$, $LiBF_4$, $LiClO_4$, etc.; linear fluoroalkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, etc. Of those, especially preferred electrolyte salts are $LiPF_6$, $LiBF_4$, LiN $(SO_2CF_3)_2$ and $LiN(SO_2C_2F_5)_2$. One alone or two or more of those electrolyte salts may be used here either singly or as combined.

A preferred combination of these electrolyte salts comprises $LiPF_6$ and contains at least one selected from $LiBF_4$, $LiN(SO_2CF_3)_2$ and $LiN(SO_2C_2F_5)_2$. Preferred are a combination of $LiPF_6$ and $LiBF_4$, a combination of $LiPF_6$ and $LiN(SO_2CF_3)_2$, a combination of $LiPF_6$ and $LiN(SO_2C_2F_5)_2$, etc.

Regarding the ratio (by mol) of $LiPF_6/[LiBF_4$ or $LiN(SO_2CF_3)_2$ or $LiN(SO_2C_2F_5)_2]$, when the ratio of $LiPF_6$ is higher than 70/30 and when the ratio of $LiPF_6$ is lower than 99/1, then the risk of worsening load characteristics after high-temperature charging storage may be low. Accordingly, the ratio (by mol) of $LiPF_6/[LiBF_4$ or $LiN(SO_2CF_3)_2$ or $LiN(SO_2C_2F_5)_2]$ is preferably within a range of from 70/30 to 99/1, more preferably within a range of from 80/20 to 98/2. Using the electrolyte salts as the combination thereof falling within the above-mentioned range is more effective for improving battery characteristics such as load characteristics after high-temperature charging storage and others.

The concentration of all these electrolyte salts as dissolved in the solution is generally preferably at least 0.3 M relative to the above-mentioned nonaqueous solvent, more preferably at least 0.5 M, even more preferably at least 0.7 M, and further preferably at least 1.1 M. The upper limit of the concentration is preferably at most 2.5 M, more preferably at most 2.0 M, even more preferably at most 1.5 M.

As the electrolyte for electric double layer capacitors (condensers), usable are known quaternary ammonium salts such as tetraethylammonium tetrafluoroborate, triethylmethylammonium tetrafluoroborate, tetraethylammonium hexafluorophosphate, etc.

[Production of Nonaqueous Electrolytic Solution]

The nonaqueous electrolytic solution of the present invention can be prepared, for example, by: mixing the nonaqueous solvents; adding the electrolyte salt to the mixture; and adding thereto the 1,2-dioxypropane compound represented by the general formula (I).

In this case, the nonaqueous solvent to be used, and the compound to be added to the electrolytic solution are preferably previously purified within a range not significantly detracting from the producibility, in which, therefore, the impurity content is preferably as low as possible.

[Electrochemical Element]

The electrochemical element of the present invention comprises a positive electrode, a negative electrode, and a nonaqueous electrolytic solution of an electrolyte salt dissolved in a nonaqueous solvent, and is characterized in that the nonaqueous electrolytic solution is the above-mentioned nonaqueous electrolytic solution of the present invention. The electrochemical element includes the following first to fourth electrochemical elements.

As the nonaqueous electrolyte, not only a liquid one but also a gelled one can be used. Further, the nonaqueous electrolytic solution of the present invention can also be used for solid polymer electrolytes. Above all, the solution is preferably used for the first electrochemical element using a lithium salt as the electrolyte salt (that is, for lithium batteries) or for the fourth electrochemical element (that is, for lithium ion capacitors), more preferably for lithium batteries, and most preferably for lithium secondary batteries.

[The First Electrochemical Element (Lithium Battery)]

The lithium battery of the present invention collectively means a lithium primary battery and a lithium secondary battery. The lithium battery of the present invention comprises a positive electrode, a negative electrode and the non-aqueous electrolytic solution of an electrolyte salt dissolved in a nonaqueous solvent. In this, the other constitutive components such as the positive electrode and the negative electrode than the nonaqueous electrolytic solution can be used with no particular limitation thereon.

(Lithium Secondary Battery)

As the positive electrode active material for the lithium secondary battery, usable is a complex metal oxide with lithium that contains at least one selected from cobalt, manganese and nickel. One kind of these positive electrode active materials can be used alone, or two or more kinds of them can be used in combination.

The lithium complex metal oxide includes, for example, $LiCoO_2$, $LiMn_2O_4$, $LiNiO_2$, $LiCo_{1-x}Ni_xO_2$ ($0.01<x<1$), $LiCo_{1/3}Ni_{1/3}Mn_{1/3}O_2$, $LiNi_{1/2}Mn_{3/2}O_4$, $LiCo_{0.98}Mg_{0.02}O_2$, etc. Combinations of $LiCoO_2$ and $LiMn_2O_4$; $LiCoO_2$ and $LiNiO_2$; $LiMn_2O_4$ and $LiNiO_2$ are acceptable herein.

For improving the safety of the battery in overcharging or improving the cycle properties thereof, or for enabling the use thereof at a charging potential of 4.3 V or more, a part of the lithium complex oxide may be substituted with any other element. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$ and $LiNiO_2$, with which the positive electrode charging potential in a fully-charged state may be 4.3 V or more based on Li. More preferred are lithium complex oxides usable at 4.4 V or more, such as $LiCo_{1-x}M_xO_2$ (where M represents at least one element of Sn, Mg, Fe, Ti, Al, Zr, Cr, V, Ga, Zn, and Cu; $0.001 \leq x \leq 0.05$), $LiCo_{1/3}Ni_{1/3}Mn_{1/3}O_2$, $LiNi_{1/2}Mn_{3/2}O_4$, and a solid solution of $Li_2MnO_3$ and $LiMO_2$ (where M represents a transition metal such as Co, Ni, Mn, Fe, etc). When a lithium complex metal oxide capable of being used at a higher charged voltage is used, the effect of improving low-temperature load characteristics after high-temperature charging storage may often worsen owing to the reaction with the electrolytic solution during charging. Of the lithium secondary battery according to the present invention, however, the battery characteristics can be prevented from worsening.

Further, as the positive electrode active material, also usable are lithium-containing olivine-type phosphates. Especially preferred are lithium-containing olivine-type phosphates containing at least one selected from iron, cobalt, nickel and manganese. Specific examples thereof include $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel, and manganese therein may be substituted with at least one element selected from Co, Mn, Ni, Mg, Al, B, Ti, V, Nb, Cu, Zn, Mo, Ca, Sr, W, Zr and the like; or the phosphates may be coated with a compound containing any of these other elements or with a carbon material. Among these, preferred are $LiFePO_4$ and $LiMnPO_4$.

Further, the lithium-containing olivine-type phosphate may be combined with, for example, the above-mentioned positive electrode active materials.

For the positive electrode for lithium primary batteries, there are mentioned oxides or chalcogen compounds of one or more metal elements such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds such as $SO_2$, $SOCl_2$, etc.;

carbon fluorides (fluorographite) represented by a general formula $(CF_x)_n$, etc. Of those, preferred are $MnO_2$, $V_2O_5$, fluorographite, etc.

Not specifically defined, the electroconductive agent of the positive electrode may be any electron-conductive material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably for use herein. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 $g/cm^3$, and for further increasing the capacity of the battery, the density is preferably at least 2 $g/cm^3$, more preferably at least 3 $g/cm^3$, even more preferably at least 3.6 $g/cm^3$. The upper limit is preferably at most 4 $g/cm^3$.

As the negative electrode active material for the lithium secondary battery, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin, tin compounds, silicon, silicon compounds and the like, either singly or as combined.

Of those, more preferred is use of high-crystalline carbon materials such as artificial graphite, natural graphite and the like, in view of the ability thereof to absorb and release lithium ions, and even more preferred is use of a carbon material having a graphite-type crystal structure where the lattice (002) spacing ($d_{002}$) is at most 0.340 nm (nanometers), especially from 0.335 to 0.337 nm.

When artificial graphite particles having a bulky structure where plural flattened graphite fine particles aggregate or bond together non-parallel to each other, or graphite particles produced through spheroidizing treatment comprising repeatedly imparting mechanical action such as compression force, friction force, shear force or the like to, for example, flaky natural graphite particles are used, and when the ratio of the peak intensity I (110) of the (110) plane of the graphite crystal obtained in X-ray diffractiometry of a negative electrode sheet as formed by pressing so that the density of the part except the collector of the negative electrode could be 1.5 $g/cm^3$ or more, to the peak intensity I (004) of the (004) plane thereof, I(110)/I(004) is at least 0.01, then the low-temperature load characteristics after high-temperature charging storage of the battery could be favorably bettered, and more preferably, the ratio is at least 0.05, even more preferably at least 0.1. On the other hand, when too much processed, then the crystallinity may worsen and the discharge capacity of the battery may lower; and therefore, the upper limit is at most 0.5, more preferably at most 0.3.

Preferably, the high-crystalline carbon material is coated with a low-crystalline carbon material, as bettering the low-temperature load characteristics after high-temperature charging storage of the battery. When the high-crystalline carbon material is used, it may react with the nonaqueous electrolytic solution in charging to thereby worsen the low-temperature load characteristics after high-temperature charging storage owing to the increase in the interfacial resistance; however, in the lithium secondary battery of the present invention, the low-temperature load characteristics after high-temperature charging storage can be bettered.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 $g/cm^3$, and for further increasing the battery capacity, the density is preferably at least 1.5 $g/cm^3$, more preferably at least 1.7 $g/cm^3$. The upper limit is preferably at most 2 $g/cm^3$.

As the negative electrode active material for lithium primary batteries, usable are lithium metal or lithium alloys.

The structure of the lithium battery is not specifically defined. The battery may be a coin-type battery, a cylindrical battery, a square-shaped battery, a laminate-type battery or the like, each having a single-layered or multi-layered separator.

For the separator for the battery, usable is a single-layer or laminate porous film of polyolefin such as polypropylene, polyethylene or the like, as well as a woven fabric, a non-woven fabric, etc.

The lithium secondary battery of the present invention has excellent low-temperature load characteristics after high-temperature charging storage even when the final charging voltage is 4.2 V or more, especially 4.3 V or more, and further, the properties of the battery are still good even at 4.4 V or more. The discharging final voltage could be generally 2.8 V or more, further 2.5 V or more; however, the discharging final voltage of the lithium secondary battery of the present invention could can be 2.0 V or more. The current value is not specifically defined, but in general, the battery is used within a range of from 0.1 to 3 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

(Lithium Primary Battery)

The constitution of the lithium primary battery is not specifically defined. Except for the constitution peculiar to lithium primary batteries, the constitution of the lithium primary battery of the present invention can be the same as that of the above-mentioned lithium secondary battery.

For the positive electrode for the lithium primary battery, there are mentioned oxides or chalcogen compounds of one or more metal elements such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds such as $SO_2$, $SOCl_2$, etc.; carbon fluorides (fluorographite) represented by a general formula $(CF_x)_n$, etc. Of those, preferred are $MnO_2$, $V_2O_5$, fluorographite, etc.

As the negative electrode active material for the lithium primary battery, usable are lithium metal, lithium alloys, etc.

[The Second Electrochemical Element (Electric Double-Layer Capacitor)]

This is an electrochemical element that stores energy by utilizing the electric double layer capacitance in the interface between the electrolytic solution and the electrode therein. One example of the present invention is an electric double layer capacitor. The most typical electrode active material to be used in the electrochemical element is active carbon.

[The Third Electrochemical Element]

This is an electrochemical element that stores energy by utilizing the doping/dedoping reaction of the electrode therein. As the electrode active material for use in the electrochemical element, there may be mentioned metal oxides such as ruthenium oxide, iridium oxide, tungsten oxide, molybdenum oxide, copper oxide, etc.; π-conjugated polymers such as polyacene, polythiophene derivatives, etc.

[The Fourth Electrochemical Element (Lithium Ion Capacitor)]

This is an electrochemical element that stores energy by utilizing the lithium ion intercalation into the carbon material such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the π-conjugated polymer electrode therein. The electrolytic solution contains at least a lithium salt such as $LiPF_6$ or the like.

[1,2-Dioxypropane Compound]

The 1,2-dioxypropane compound of the present invention is represented by the following general formula (II):

[Chemical Formula 4]

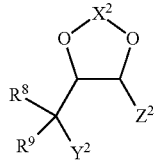

(II)

(In the formula, $R^8$ and $R^9$ each represent a hydrogen atom, or an alkyl group having from 1 to 6 carbon atoms; $X^2$ represents a group selected from —S(=O)—, —S(=O)$_2$—, —C(=O)—, —P(=O)(OR$^{10}$)— and —SiR$^{11}$R$^{12}$—; $R^{10}$ to $R^{12}$ each represent an alkyl group having from 1 to 6 carbon atoms.

$Y^2$ represents an alkylsulfinyl group having from 1 to 4 carbon atoms, an alkenylsulfinyl group having from 2 to 6 carbon atoms, an alkynylsulfinyl group having from 3 to 6 carbon atoms, an alkylsulfonyl group having from 1 to 4 carbon atoms, an alkenylsulfonyl group having from 2 to 6 carbon atoms, or an alkynylsulfonyl group having from 3 to 6 carbon atoms;

$Z^2$ represents a hydrogen atom, a methyl group, an alkylsulfinylmethyl group having from 2 to 7 carbon atoms, an alkylsulfinylmethyl group having from 2 to 7 carbon atoms, an alkenylsulfinylmethyl group having from 3 to 7 carbon atoms, an alkynylsulfinylmethyl group having from 4 to 7 carbon atoms, an alkylsulfonylmethyl group having from 2 to 7 carbon atoms, an alkenylsulfonylmethyl group having from 3 to 7 carbon atoms, or an alkynylsulfonylmethyl group having from 4 to 7 carbon atoms.

At least one hydrogen atom on the carbon atom of $X^2$, $Y^2$ and $Z^2$ may be substituted with a halogen atom.)

Specific examples and preferred examples of the 1,2-dioxypropane compound represented by the general formula (II) are the same as those mentioned hereinabove for the general formula (I).

The 1,2-dioxypropane compound represented by the general formula (I) can be produced according to the following method, to which, however, the present invention is not limited. The starting material, diol compound having $X^1$ and $Y^1$ (hereinafter simply referred to as "diol compound") can be produced according to already-existing general methods. For example, according to the method described in Bulletin of the Chemical Society of Japan, 1995, vol. 68, No. 1, pp. 227-229, a commercial compound, 3-mercaptopropane-1,2-diol is alkylated to give a 3-(alkylthiopropane)-1,2-diol; and then according to the method described in Journal of Organic Chemistry, 1982, Vol. 47, No. 19, pp. 3660-3664, this is oxidized to give a 3-(alkynylsulfonyl)propane-1,2-diol.

(a) For producing the compound where $X^1$ is —S(=O)—, there is mentioned a method of reacting the diol compound with a thionyl halide such as thionyl chloride, thionyl bromide or the like in a solvent or in the absence of a solvent, and in the presence or absence of a base.

(b) For producing the compound where $X^1$ is —C(=O)—, there are mentioned a method of reacting the diol compound with triphosgene, carbonyldiimidazole or the like in a solvent or in the absence of a solvent, and in the presence or absence of a base; a method of transesterifying the diol compound with a carbonate ester in a solvent or in the absence of a solvent, and in the presence of an acid or base catalyst.

(c) For producing the compound where $X^1$ is $CR^3R^4$, there is mentioned a method of reacting the diol compound with a carbonyl compound such as aldehyde, ketone or the like, or with a carbonyl-equivalent compound such as acetal, ketal or the like in a solvent or in the absence of a solvent, and in the presence of an acid catalyst.

(d) For producing the compound where $X^1$ is —P(=O)(OR$^{10}$)—, there is mentioned a method of reacting the diol compound with a dihalogenophosphoric acid alkyl ester such as a dichlorophosphoric acid alkyl ester, a dibromophosphoric acid alkyl ester or the like in a solvent or in the absence of a solvent, in the presence or absence of a base, and in the presence or absence of a catalyst.

(e) For producing the compound where $X^1$ is —SiR$^{11}$R$^{12}$—, there is mentioned a method of reacting the diol compound with a dihalogenodialkylsilane such as a dibromodialkylsilane or the like in a solvent or in the absence of a solvent and in the presence or absence of a base.

(f) For producing the compound where $X^1$ is —S(=O)$_2$—, there are mentioned a method of reacting the compound produced in the above (a), with an oxidizing agent in a solvent or in the absence of a solvent and in the presence or absence of a catalyst, and a method of reacting the diol with sulfuryl chloride in a solvent or in the absence of a solvent and in the presence or absence of a base.

In the production methods (a) and (b), the amount of the thionyl chloride, triphosgene, carbonyldiimidazole or the like to be reacted with the diol compound (for triphosgene, the amount is a phosgene-equivalent one) is preferably from 0.8 to 10 mol, more preferably from 1 to 5 mol, even more preferably from 1 to 3 mol relative to 1 mol of the diol.

The solvent to be used for the production is not specifically defined and may be any one inert to the reaction. The usable solvent includes aliphatic hydrocarbons, halogenohydrocarbons, aromatic hydrocarbons, halogenoaromatic hydrocarbons, ethers, esters, carbonates, etc. Of those, preferred are aromatic hydrocarbons such as toluene, xylene, etc.; halogenohydrocarbons such as methylene chloride, 1,2-dichloroethane, etc. The amount of the solvent to be used is preferably from 0 to 30 parts by weight relative to 1 part by weight of the diol compound, more preferably from 1 to 15 parts by weight.

As the base for use for the production, any of an inorganic base or an organic base is usable. These may be used either singly or as combined. The usable inorganic base includes potassium carbonate, sodium carbonate, calcium hydroxide, calcium oxide, etc. The usable organic base includes linear or branched aliphatic tertiary amines, and unsubstituted or substituted imidazole, pyridine and pyrimidine. More preferred are trialkylamines such as trimethylamine, triethylamine, tripropylamine, tributylamine, diisopropylethylamine, etc.; and pyridines such as pyridine, N,N-dimethylaminopyridine, etc.

The amount of the base to be used may be from 1.6 to 20 mol relative to 1 mol of the diol, more preferably from 2 to 10 mol, even more preferably from 2 to 8 mol.

In the above-mentioned reaction, the lower limit of the reaction temperature is preferably −30° C. or higher, and is more preferably −10° C. or higher so as not to lower the reactivity. The upper limit of the reaction temperature is preferably 100° C. or lower, more preferably 80° C. or lower, from the viewpoint of preventing side reaction and decomposition of product.

The reaction time may vary depending on the reaction temperature and the scale, however, when the reaction time is too short, then unreacted matters may remain, but on the contrary, when the reaction time is too long, the reaction product may be decomposed and side reaction may occur. Preferably, therefore, the reaction time is from 0.1 to 24 hours, more preferably from 0.5 to 12 hours.

In the production method (b), the carbonate ester to be used for transesterification with the diol may be any of linear or cyclic carbonate esters. The usable linear carbonate ester includes dimethyl carbonate, diethyl carbonate, dipropyl carbonate, dibutyl carbonate, methyl ethyl carbonate, diisopropyl carbonate, diphenyl carbonate, etc.; and the usable cyclic carbonate ester includes ethylene carbonate, propylene carbonate, etc. From the viewpoint of removing the by-produced alcohol out of the system to thereby promote the reaction, preferred are carbonate esters composed of a low-boiling point alcohol, such as dimethyl carbonate, diethyl carbonate, methyl ethyl carbonate, etc.

The amount of the carbonate ester to be used is preferably from 1 to 20 mol relative to 1 mol of the diol compound, more preferably from 1 to 10 mol, even more preferably from 1 to 5 mol.

As the catalyst for use in the reaction, any of an acid catalyst or a base catalyst is usable. The usable acid catalyst includes mineral acids such as sulfuric acid, phosphoric acid, etc.; sulfonic acids such as paratoluenesulfonic acid, metanesulfonic acid, trifluoromethanesulfonic acid, etc.; Lewis acids such as trifluoroboric acid, tetraisopropoxytitanium, etc.; solid acids such as zeolite, acid resin, etc.; and their mixed acids. Especially preferred are sulfonic acids such as paratoluenesulfonic acid, metanesulfonic acid, trifluoromethanesulfonic acid, etc.; and Lewis acids such as tetraisopropoxytitanium, etc. The base usable here includes metal alkoxides such as sodium methylate, sodium ethylate, potassium tert-butoxide, etc.; metal hydrides such as sodium hydride, potassium hydride, etc.; alkali metals such as sodium, potassium, lithium, etc.; and their mixtures. Especially preferred are metal alcoholates such as sodium methylate, sodium ethylate, potassium tert-butoxide, etc.

The amount of the catalyst to be used is preferably from 0.001 to 5 mol relative to 1 mol of the diol, more preferably from 0.01 to 1 mol, even more preferably from 0.01 to 0.3 mol, from the viewpoint of preventing side reaction.

In the above-mentioned reaction, the lower limit of the reaction temperature is preferably 0° C. or higher, and so as not to lower the reactivity, the temperature is more preferably 20° C. or higher. The upper limit of the reaction temperature is preferably 200° C. or lower, and so as to prevent side reaction and decomposition of the product, the temperature is more preferably 150° C. or lower. The reaction time varies depending on the reaction temperature and the scale, however, when the reaction time is too short, then unreacted matters may remain, but on the contrary, when the reaction time is too long, the reaction product may be decomposed and side reaction may occur. Preferably, therefore, the reaction time is from 0.1 to 24 hours, more preferably from 0.2 to 15 hours.

EXAMPLES

Synthesis Examples of the 1,2-dioxypropane compound of the present invention, and Examples of the nonaqueous electrolytic solution using the compound are shown below. However, the present invention is not limited to these Examples.

Synthesis Example 1

Synthesis of 4-(methylsulfonylmethyl)-1,3,2-dioxathiolane-2-oxide 9.00 g (58.4 mmol) of 3-(methylsulfonyl)propane-1,2-diol was dissolved in 100 mL of methylene chloride. 7.64 g (64.2 mmol) of thionyl chloride was dropwise added to the solution at an inner temperature of from 20 to 25° C. After this was stirred at 35° C. for 2 hours, the solvent and the remaining thionyl chloride were evaporated away under reduced pressure to give 11.40 g of a crude crystal. The obtained crude crystal was recrystallized from dimethyl carbonate/2-propanol to give 6.60 g of the intended 4-(methylsulfonylmethyl)-1,3,2-dioxathiolane-2-oxide as a diastereomeric mixture (mixture ratio 9/1) (yield 56%).

The obtained 4-(methylsulfonylmethyl)-1,3,2-dioxathiolane-2-oxide was analyzed through $^1$H-NMR and mass spectrometry and its melting point was measured, thereby identifying the structure thereof. The results are shown below.

(1)$^1$H-NMR (300 MHz, CDCl$_3$): δ=5.48-5.40 (m, 0.9H), 5.12-5.03 (m, 0.1H), 4.92 (dd, J=4.92, 6.34 Hz, 0.9H), 4.75-4.59 (m, 0.2H), 4.39-4.34 (m, 0.9H), 3.82-3.17 (m, 2H), 3.08 (d, J=0.73, 0.3H), 3.06 (d, J=0.73, 2.7H).

(2) MS(CI): m/z=201 (M+1).

(3) Melting point: 52-55° C.

Synthesis Example 2

Synthesis of 4-(methylsulfonylmethyl)-1,3-dioxolan-2-one 5.70 g (37.0 mmol) of 3-(methylsulfonyl)propane-1,2-diol and 17.56 g (220.0 mol) of pyridine were dissolved in 100 mL of methylene chloride, and 20 mL of a toluene solution of 10.97 g (37.0 mmol) of triphosgene was dropwise added to the solution at an inner temperature of from 5° C. to 15° C., taking 30 minutes, and stirred at room temperature for 1 hour. 20 mL of water was added thereto for liquid-liquid separation, and the organic layer was dried with magnesium sulfate and concentrated under reduced pressure. The residue was recrystallized from dimethyl carbonate/acetonitrile to give 1.30 g of the intended 4-(methylsulfonylmethyl)-1,3-dioxolan-2-one (yield 20%).

(1)$^1$H-NMR (300 MHz, CD$_3$CN): δ=5.22-5.13 (m, 1H), 4.68-4.62 (m, 1H), 4.27 (dd, J=8.79, 7.07 Hz, 1H), 3.72-3.64 (m, 1H), 3.42-3.35 (m, 1H), 2.99-2.98 (m, 3H).

(2) MS(CI): m/z=181 (M+1).

(3) Melting point: 118-120° C.

Examples 1 to 14, Comparative Examples 1 to 3

Production of Lithium Ion Secondary Battery

94% by mass of LiNi$_{1/3}$Mn$_{1/3}$Co$_{1/3}$O$_2$ and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and cutted into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and cutted into a predetermined size, thereby producing a negative electrode sheet. The density of the part of the negative electrode except the collector was 1.5 g/cm$^3$. The electrode sheet was analyzed through X-ray diffractiometry, and I(110)/I(004) thereof was 0.1. The positive electrode sheet, a porous polyethylene film separator and the negative electrode sheet were laminated in that order, and the nonaqueous electrolytic solution having the composition shown in Table 1 was added thereto to construct a 2032 coin-type battery.

The compounds used in the nonaqueous electrolytic solution in Examples 1 to 14 and Comparative Examples 2 to 3 are shown below.

[Chemical Formula 5]

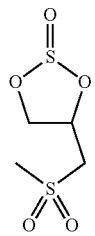

[1]

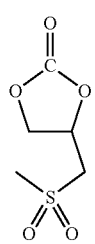

[2]

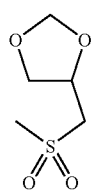

[3]

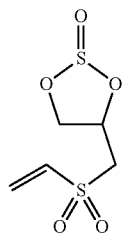

[4]

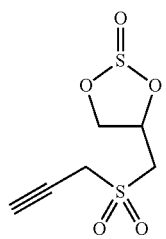

[5]

-continued

[6]
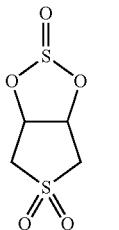

[Compound in Comparative Example 3]

[7] [Evaluation of Low-Temperature Load Characteristics after High-Temperature Charging Storage]

(1) Initial Discharge Capacity

In a thermostatic chamber kept at 25° C., the coin-type battery fabricated according to the above-mentioned method was charged up to a final voltage of 4.3 V for 3 hours with a constant current of 1 C and under a constant voltage, then the temperature of the thermostatic chamber was lowered to 0° C., and the battery was discharged under a constant current of 1 C to a final voltage of 2.75 V. The initial discharge capacity at 0° C. was measured.

(2) High-Temperature Charging Storage Test

Next, in a thermostatic chamber at 60° C., the coin-type battery was charged up to a final voltage of 4.3 V for 3 hours with a constant current of 1 C and under a constant voltage, and then stored for 3 days while kept at 4.3 V. Subsequently, this was put in a thermostatic chamber at 25° C., and once discharged under a constant current of 1 C to a final voltage of 2.75 V.

(3) Discharge Capacity after High-Temperature Charging Storage

Further after that, the discharge capacity at 0° C. after high-temperature charging storage was measured in the same manner as that for the measurement of the initial discharge capacity.

(4) Low-Temperature Load Characteristics after High-Temperature Charging Storage The low-temperature load characteristics after high-temperature charging storage were determined based on the 0° C. discharge capacity retention rate mentioned below.

0° C. Discharge Capacity Retention Rate after high-temperature charging storage (%)=(discharge capacity at 0° C. after high-temperature charging storage/initial discharge capacity at 0° C.)×100.

The condition in producing the batteries and the battery characteristics are shown in Table 1.

[Table 1]

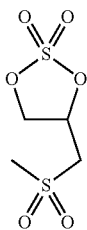
[Chemical Formula 6]

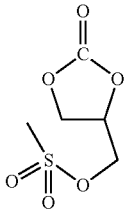
[Compound in Comparative Example 2]

TABLE 1

|  | Composition of Electrolyte Salt Composition of Nonaqueous Electrolytic Solution (ratio by volume of solvents) | Compound [Compound Number] | Amount Added (content in nonaqueous electrolytic solution) (wt %) | 0° C. Discharge Capacity Retention Rate after high-temperature charging storage (%) |
|---|---|---|---|---|
| Example 1 | 1.2M LiPF6 EC/FEC/MEC/DMC (20/10/50/20) | 4-(methylsulfonylmethyl)-1,3,2-dioxathiolane-2-oxide [1] | 0.1 | 75 |
| Example 2 | 1.2M LiPF6 EC/FEC/MEC/DMC (20/10/50/20) | 4-(methylsulfonylmethyl)-1,3,2-dioxathiolane-2-oxide [1] | 1 | 83 |
| Example 3 | 1.2M LiPF6 EC/FEC/MEC/DMC (20/10/50/20) | 4-(methylsulfonylmethyl)-1,3,2-dioxathiolane-2-oxide [1] | 4 | 80 |
| Example 4 | 1.2M LiPF6 EC/FEC/MEC/DMC (20/10/50/20) | 4-(methylsulfonylmethyl)-1,3,2-dioxathiolane-2-oxide [1] | 7 | 77 |

TABLE 1-continued

| | Composition of Electrolyte Salt Composition of Nonaqueous Electrolytic Solution (ratio by volume of solvents) | Compound [Compound Number] | Amount Added (content in nonaqueous electrolytic solution) (wt %) | 0° C. Discharge Capacity Retention Rate after high-temperature charging storage (%) |
|---|---|---|---|---|
| Example 5 | 1.2M LiPF6 EC/FEC/MEC/DMC (20/10/50/20) | 4-(methylsulfonylmethyl)-1,3-dioxolan-2-one [2] | 1 | 81 |
| Example 6 | 1.2M LiPF6 EC/FEC/MEC/DMC (20/10/50/20) | 4-(methylsulfonylmethyl)-1,3-dioxolane [3] | 1 | 80 |
| Example 7 | 1.2M LiPF6 EC/FEC/MEC/DMC (20/10/50/20) | 4-(vinylsulfonylmethyl)-1,3,2-dioxathiolane-2-oxide [4] | 1 | 77 |
| Example 8 | 1.2M LiPF6 EC/FEC/MEC/DMC (20/10/50/20) | 4-(2-propynylsulfonylmethyl)-1,3,2-dioxathiolane-2-oxide [5] | 1 | 76 |
| Example 9 | 1.2M LiPF6 EC/FEC/MEC/DMC (20/10/50/20) | tetrahydro-thieno[3,4-d]-1,3,2-dioxathiolane-2,5,5-trioxide [6] | 1 | 76 |
| Example 10 | 1.2M LiPF6 EC/FEC/MEC/DMC (20/10/50/20) | 2-methoxy-4-(methylsulfonylmethyl)-1,3,2-dioxaphospholane-2-oxide [7] | 1 | 74 |
| Example 11 | 1.2M LiPF6 EC/FEC/MEC/DMC (20/10/50/20) | 4-(methylsulfonylmethyl)-1,3,2-dioxathiolane-2,2-dioxide [8] | 1 | 73 |
| Example 12 | 1.2M LiPF6 EC/FEC/MEC/DMC (20/10/50/20) | 2,2-dimethyl-4-(methylsulfonylmethyl)-1,3,2-dioxasilolane [9] | 1 | 72 |
| Example 13 | 1M LiPF6 EC/PC/VC/DMC (23/5/2/70) | 4-(methylsulfonylmethyl)-1,3,2-dioxathiolane-2-oxide [1] | 1 | 80 |
| Example 14 | 1.2M LiPF6 EC/VC/FEC/MEC/DMC (10/1/14/50/25) | 4-(methylsulfonylmethyl)-1,3,2-dioxathiolane-2-oxide [1] | 1 | 85 |
| Comparative Example 1 | 1M LiPF6 EC/FEC/MEC/DMC (20/10/50/20) | none | — | 62 |
| Comparative Example 2 | 1.2M LiPF6 EC/FEC/MEC/DMC (20/10/50/20) | 4-(methanesulfonyloxymethyl)-1,3-dioxolan-2-one | 1 | 61 |
| Comparative Example 3 | 1.2M LiPF6 EC/FEC/MEC/DMC (20/10/50/20) | erythritan sulfite | 1 | 63 |

Example 15, Comparative Example 4

A negative electrode sheet was produced, using Si (negative electrode active material) in place of the negative electrode active material used in Example 2 and Comparative Example 1. Precisely, 80% by mass of Si and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and cutted into a predetermined size, thereby producing a negative electrode sheet. Coin-type batteries were produced and evaluated in the same manner as in Example 2 and Comparative Example 1, except that the negative electrode sheet produced herein was used. The results are shown in Table 2.

[Table 2]

TABLE 2

| | Composition of Electrolyte Salt Composition of Nonaqueous Electrolytic Solution (ratio by volume of solvents) | Compound [Compound Number] | Amount Added (content in nonaqueous electrolytic solution) (wt %) | 0° C. Discharge Capacity Retention Rate after high-temperature charging storage (%) |
|---|---|---|---|---|
| Example 15 | 1.2M LiPF6 EC/FEC/MEC/DMC (20/10/50/20) | 4-(methylsulfonylmethyl)-1,3,2-dioxathiolane-2-oxide [1] | 1 | 71 |
| Comparative Example 4 | 1.2M LiPF6 EC/FEC/MEC/DMC (20/10/50/20) | none | — | 53 |

Example 16, Comparative Example 5

A positive electrode sheet was produced by changing the positive electrode active material used in Example 2 and Comparative Example 1 to LiFePO$_4$ (positive electrode active material) coated with amorphous carbon. Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and cutted into a predetermined size, thereby producing a positive electrode sheet. Coin-type batteries were produced and evaluated in the same manner as in Example 2 and Comparative Example 1, except that the positive electrode sheet thus produced herein was used and that, in battery evaluation, the charging final voltage was changed to 3.6 V and the discharging final voltage was changed to 2.0 V. The results are shown in Table 3.

[Table 3]

TABLE 3

| | Composition of Electrolyte Salt Composition of Nonaqueous Electrolytic Solution (ratio by volume of solvents) | Compound [Compound Number] | Amount Added (content in nonaqueous electrolytic solution) (wt %) | 0° C. Discharge Capacity Retention Rate after high-temperature charging storage (%) |
|---|---|---|---|---|
| Example 16 | 1.2M LiPF6 EC/FEC/MEC/DMC (20/10/50/20) | 4-(methylsulfonylmethyl)-1,3,2-dioxathiolane-2-oxide [1] | 1 | 83 |
| Comparative Example 5 | 1.2M LiPF6 EC/FEC/MEC/DMC (20/10/50/20) | none | — | 69 |

The lithium secondary batteries of Examples 1 to 14 were all remarkably bettered in point of the low-temperature load characteristics after high-temperature charging storage, as compared with the lithium secondary battery of Comparative Example to which the 1,2-dioxypropane compound represented by the general formula (I) was not added (Comparative Example 1), the lithium secondary battery of Comparative Example to which was added 4-(methanesulfonyloxymethyl)-1,3-dioxolan-2-one having an oxysulfonyl group at the 4-position of the 5-membered ring structure via a carbon atom therebetween (Comparative Example 2), and the lithium secondary battery of Comparative Example to which was added erythritan sulfite having an ether oxygen at the 4-position of the 5-membered ring structure via a carbon atom therebetween (Comparative Example 3).

From the above, it has been confirmed that the effect of the present invention is unique to the specific compound having a structure where a sulfinyl group or a sulfonyl group bonds to the 4-position of a 5-membered ring structure having a specific substituent, via a carbon atom therebetween.

In addition, from comparison between Example 15 and Comparative Example 4, and from comparison between Example 16 and Comparative Example 5, the same effect is seen in the case where Si was used as the negative electrode and in the case where a lithium-containing olivine-type iron phosphate was used as the positive electrode. Accordingly, it is obvious that the effect of the present invention does not depend on any specific positive electrode or negative electrode.

Further, the nonaqueous electrolytic solution of the present invention has an effect of improving the low-temperature load characteristics after high-temperature storage of lithium primary batteries.

INDUSTRIAL APPLICABILITY

Using the nonaqueous electrolytic solution of the present invention provides electrochemical elements such as lithium batteries and the like excellent in low-temperature load characteristics after high-temperature charging storage.

The invention claimed is:

1. A nonaqueous electrolytic comprising an electrolyte salt dissolved in a nonaqueous solvent and a 1,2-dioxypropane compound represented by formula (I) in an amount of from 0.001 to 20% by mass of the nonaqueous electrolytic solution:

(I)

wherein $R^1$ and $R^2$ each represent a hydrogen atom, or an alkyl group having from 1 to 6 carbon atoms;
$X^1$ represents a group selected from the group consisting of —S(=O)—, —S(=O)$_2$—, —C(=O)—, —CR$^3$R$^4$—, —P(=O)(OR$^5$)— and —SiR$^6$R$^7$—; $R^3$ and $R^4$ each represent a hydrogen atom, or an alkyl group having from 1 to 6 carbon atoms; $R^5$ to $R^7$ each represent an alkyl group having from 1 to 6 carbon atoms;
$Y^1$ represents an alkylsulfinyl group having from 1 to 6 carbon atoms, an alkenylsulfinyl group having from 2 to 6 carbon atoms, an alkynylsulfinyl group having from 3 to 6 carbon atoms, an arylsulfinyl group having from 6 to 12 carbon atoms, an alkylsulfonyl group having from 1 to 6 carbon atoms, an alkenylsulfonyl group having from 2 to 6 carbon atoms, an alkynylsulfonyl group having from 3 to 6 carbon atoms, or an arylsulfonyl group having from 6 to 12 carbon atoms;
$Z^1$ represents a hydrogen atom, an alkyl group having from 1 to 4 carbon atoms, an alkylsulfinylmethyl group having from 2 to 7 carbon atoms, an alkenylsulfinylmethyl group having from 3 to 7 carbon atoms, an alkynylsulfinylmethyl group having from 4 to 7 carbon atoms, an arylsulfinylmethyl group having from 7 to 13 carbon atoms, an alkylsulfonylmethyl group having from 2 to 7 carbon atoms, an alkenylsulfonylmethyl group having from 3 to 7 carbon atoms, an alkynylsulfonylmethyl group having from 4 to 7 carbon atoms, or an arylsulfonylmethyl group having from 7 to 13 carbon atoms.

2. The nonaqueous electrolytic solution of claim 1, wherein $R^1$ and $R^2$ each represent a hydrogen atom, or an alkyl group having from 1 to 4 carbon atoms.

3. The nonaqueous electrolytic solution of claim 1, wherein $X^1$ is a group —S(=O)— or —C(=O)—.

4. The nonaqueous electrolytic solution of claim 1, wherein $Y^1$ is a methylsulfinyl group, an ethylsulfinyl group, a vinylsulfinyl group, a 2-propenylsulfinyl group, a methylsulfonyl group, an ethylsulfonyl group, a vinylsulfonyl group, a 2-propenylsulfonyl group, or a 2-propynylsulfonyl group.

5. The nonaqueous electrolytic solution of claim 1, wherein $Z^1$ is a hydrogen atom, a methyl group, a methylsulfinylmethyl group, an ethylsulfinylmethyl group, a vinylsulfinylmethyl group, a 2-propenylsulfinylmethyl group, a methylsulfonylmethyl group, an ethylsulfonylmethyl group, a vinylsulfonylmethyl group, a 2-propenylsulfonylmethyl group, or a 2-propynylsulfonylmethyl group.

6. The nonaqueous electrolytic solution of claim 1, wherein a halogen atom with which the hydrogen atom on the carbon atom of $X^1$, $Y^1$ and $Z^1$ is substituted is a fluorine atom or a chlorine atom.

7. The nonaqueous electrolytic solution of claim 1, wherein the 1,2-dioxypropane compound is at least one selected from the group consisting of 4-(methylsulfonylmethyl)-1,3,2-dioxathiolane-2-oxide, 4-(methylsulfonylmethyl)-1,3-dioxolan-2-one, 4-(methylsulfonylmethyl)-1,3-dioxolane, tetrahydro-thieno[3,4-d]-1,3,2-dioxathiolane-2,5,5-trioxide, 4-(vinylsulfonylmethyl)-1,3,2-dioxathiolane-2-oxide, 2-methoxy-4-(methylsulfonylmethyl)-1,3,2-dioxaphospholane-2-oxide, 4-(methylsulfonylmethyl)-1,3,2-dioxathiolane-2,2-dioxide, and 2,2-dimethyl-4-(methylsulfonylmethyl)-1,3,2-dioxasilolane.

8. The nonaqueous electrolytic solution of claim 1, wherein the nonaqueous solvent comprises a cyclic carbonate.

9. The nonaqueous electrolytic solution of claim 8, wherein the cyclic carbonates is at least one selected from the group consisting of ethylene carbonate, propylene carbonate, 1,2-butylene carbonate, 2,3-butylene carbonate, 4-fluoro-1,3-dioxolan-2-one, trans or cis-4,5-difluoro-1,3-dioxolan-2-one, vinylene carbonate, and vinylethylene carbonate.

10. The nonaqueous electrolytic solution of claim 1, wherein the nonaqueous solvent comprises a linear carbonate.

11. The nonaqueous electrolytic solution of claim 10, wherein the linear carbonates is at least one selected from the group consisting of methyl ethyl carbonate, methyl propyl carbonate, methyl isopropyl carbonate, methyl butyl carbonate, and ethyl propyl carbonate.

12. The nonaqueous electrolytic solution of claim 10, wherein the nonaqueous solvent further comprises a cyclic carbonate and a ratio of cyclic carbonate/linear carbonate (by volume) is from 10/90 to 40/60.

13. The nonaqueous electrolytic solution of claim 1, wherein the nonaqueous solvent comprises at least one selected from the group consisting of a linear ester, a lactone, an ether, an amide, a phosphate, a sulfone, a nitrile, a S=O bond-containing compound, a linear carboxylic acid anhydride, a cyclic acid anhydride, a cyclic phosphazene compound and an aromatic compound.

14. The nonaqueous electrolytic solution of claim 1, wherein the electrolyte salt comprises at least one lithium salt selected from the group consisting of $LiPF_6$, $LiPO_2F_2$, $LiBF_4$, $LiClO_4$, $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, $(CF_2)_2(SO_2)_2NLi$, $(CF_2)_3(SO_2)_2NLi$, lithium bis[oxalate-O,O']borate, and lithium difluoro[oxalate-O,O']borate.

15. The nonaqueous electrolytic solution of claim 14, wherein the lithium salt comprises $LiPF_6$ and at least one selected from the group consisting of $LiBF_4$, $LiN(SO_2CF_3)_2$ and $LiN(SO_2C_2F_5)_2$.

16. The nonaqueous electrolytic solution of claim 1, wherein the concentration of electrolyte salts is from 0.3 to 2.5 M relative to the nonaqueous solvent.

17. An electrochemical element comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of claim 1.

18. The electrochemical element of claim 17, wherein a positive electrode active material is a complex metal oxide with lithium that contains at least one selected from the group consisting of cobalt, manganese and nickel, or lithium-containing olivine-type phosphates containing at least one selected from the group consisting of iron, cobalt, nickel and manganese.

19. The electrochemical element of claim 17, wherein a negative electrode active material comprises at least one selected from the group consisting of lithium metal, a lithium alloy, a carbon material capable of absorbing and releasing lithium, tin, a tin compound, silicon, and a silicon compound.

* * * * *